US008685662B2

(12) United States Patent
Pied et al.

(10) Patent No.: US 8,685,662 B2
(45) Date of Patent: Apr. 1, 2014

(54) USE OF THE α CHAIN OF BRAIN SPECTRIN AND FRAGMENTS THEREOF, FOR DIAGNOSING CEREBRAL DISEASES

(75) Inventors: Sylviane Pied, Paris (FR); Vincent Guiyedi, Evry (FR); Pierre-André Cazenave, Paris (FR); Maryvonne Kombila, Libreville (GA); Youri Chanseaud, La Courneuvue (FR)

(73) Assignees: Institut Pasteur, Paris (FR); Universite Pierre et Marie Curie (Paris 6), Paris (FR)

( * ) Notice: Subject to any disclaimer, the term of this patent is extended or adjusted under 35 U.S.C. 154(b) by 761 days.

(21) Appl. No.: 12/295,435

(22) PCT Filed: Mar. 30, 2007

(86) PCT No.: PCT/IB2007/001679
§ 371 (c)(1),
(2), (4) Date: Aug. 9, 2010

(87) PCT Pub. No.: WO2007/113685
PCT Pub. Date: Oct. 11, 2007

(65) Prior Publication Data
US 2010/0304408 A1     Dec. 2, 2010

(30) Foreign Application Priority Data

Mar. 30, 2006  (EP) .................................... 06290503

(51) Int. Cl.
| | | |
|---|---|---|
| G01N 33/53 | (2006.01) | |
| G01N 33/532 | (2006.01) | |
| G01N 33/535 | (2006.01) | |
| G01N 33/536 | (2006.01) | |
| G01N 33/543 | (2006.01) | |
| G01N 33/564 | (2006.01) | |
| G01N 33/569 | (2006.01) | |
| C07K 16/18 | (2006.01) | |
| A61K 38/17 | (2006.01) | |
| C07K 14/435 | (2006.01) | |

(52) U.S. Cl.
USPC ......... 435/7.92; 435/7.1; 435/7.21; 435/7.93; 435/7.94; 435/7.95; 436/506; 436/518; 436/519; 436/524; 436/528; 436/531; 436/534; 436/536; 436/543; 436/544; 436/164; 436/172; 436/811; 530/324; 530/350; 530/388.2; 530/389.1; 530/391.1; 530/391.3; 530/403; 530/806; 530/810; 530/839

(58) Field of Classification Search
USPC ............... 435/7.1, 7.21, 7.8, 7.92, 7.93, 7.94, 435/7.95, 331, 332, 973, 975; 436/506, 436/518, 519, 524, 528, 531, 534, 536, 543, 436/544, 548, 15, 164, 172, 811, 8; 530/324, 325, 326, 327, 328, 329, 350, 530/388.2, 389.1, 391.1, 391.3, 403, 806, 530/810, 839
See application file for complete search history.

(56) References Cited

U.S. PATENT DOCUMENTS

| | | | | |
|---|---|---|---|---|
| 7,456,027 B2 * | 11/2008 | Wang et al. | .................... | 436/503 |
| 2005/0260697 A1 | 11/2005 | Wang et al. | | |

FOREIGN PATENT DOCUMENTS

| | | |
|---|---|---|
| JP | 07 198717 | 8/1995 |
| WO | 02 46767 | 6/2002 |
| WO | 2004 025298 | 3/2004 |
| WO | 2005/106038 | * 11/2005 |
| WO | 2005 106038 | 11/2005 |

OTHER PUBLICATIONS

Berzins et al., 1983. Studies on the specificity of anti-erythrocyte antibodies in the serum of patients with malaria. Clinical Exp. Immunology 54: 313-318.*
Saido et al., 1993. Spatial resolution of fodrin proteolysis in postischemic brain. J. Biol. Chem. 268: 25239-25243.*
Shukla et al., "Activation of calpains, calpastatin and spectrin cleavage in the brain during the patholgy of fatal murine cerebral malaria", Neurochemistry iInternational, vol. 48, No. 2, pp. 108-113, 2006.
Day et al., "The Prognostic and Pathophysiologic Role of Pro- and Antiinflammatory Cytokines in Severe Malaria", XP002397587, vol. 180, No. 4, pp. 1288-1297, 1999.
Vazquez et al., "Antibodies to human brain spectrin in Alzheimer's disease", Journal of Neuroimmunolgy, vol. 68, No. 1-2, pp. 39-44, 1996.
Guiyedi et al., "Self-Reactivities to the Non-Erythroid Alpha Spectrin Correlate with Cerebral Malaria in Gabonese Children", Plos One, vol. 2, No. 4, pp. 1-10, 2007.

* cited by examiner

*Primary Examiner* — Mark Shibuya
*Assistant Examiner* — James L Grun
(74) *Attorney, Agent, or Firm* — Oblon, Spivak, McClelland, Maier & Neustadt, L.L.P.

(57) ABSTRACT

The present invention pertains to a method for in vitro prognosticating and/or diagnosing cerebral cerebral malaria, wherein said method comprises a step of detecting non-erythroid spectrin or fragments thereof, and/or antibodies directed against non-erythroid spectrin, in a biological sample. Reagents and kits for performing this method are also disclosed.

5 Claims, 9 Drawing Sheets

Figure 1:
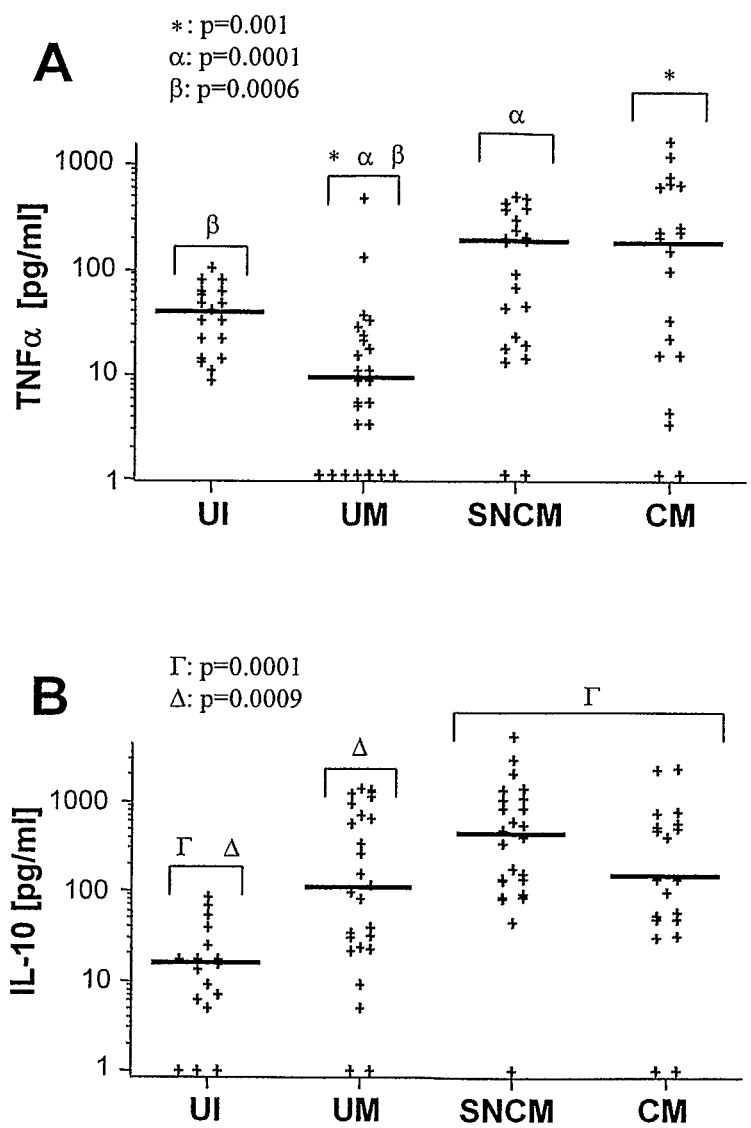

USE OF THE α CHAIN OF BRAIN SPECTRIN AND FRAGMENTS THEREOF, FOR DIAGNOSING CEREBRAL DISEASES

CROSS-REFERENCE TO RELATED APPLICATIONS

The present application is a 35 U.S.C. §371 National Stage patent application of International patent application PCT/IB2007/001679, filed on Mar. 30, 2007, which claims priority to European patent application EP 06290503.9, filed on Mar. 30, 2006.

The present invention relates to the fields of cerebral diseases and of malaria control. More particularly, the invention concerns a method for performing an in vitro prognosis and/or diagnosis of cerebral malaria, in order to quickly provide an appropriate treatment to a patient in need thereof.

Malaria remains one of the leading causes of death in most of sub-Saharian Africa, and mortality rates are particularly high for children under the age of five years, pregnant women and immunodeficient individuals (1). Fatal outcome occurs nearly exclusively in patients infected with *Plasmodium falciparum* who progress to severe malaria (1, 2). Severe anemia and cerebral malaria (CM) are the most prevalent types of severe *P. falciparum* malaria, and CM displays the more acute clinical spectrum. Patients who develop CM present with a range of acute neurological manifestation and the pathology is characterized by a diffuse encephalopathy, alteration in levels of consciousness, deep coma and seizure preceding death (2, 3). At present, the pathological events leading to fatal malaria in humans are not well characterized. Gaining an understanding of the mechanisms involved is a major challenge, as it will be crucial to the development of new preventive or curative therapies and/or vaccines, and it might lead to defining prognostic markers.

In CM, the sequestration of mature *P. falciparum*-infected red blood cells to the cerebral endothelium is clearly a central event in the pathogenesis. One of the factors thought to influence clinical outcome is the fine balance between the pro- and anti-inflammatory cytokines produced during the infection and that modulate parasite-induced immune responses (4, 5). Pro-inflammatory cytokines, such as interferon γ (IFNγ) and tumor necrosis factor α (TNFα), are known to play an important role in CM physiopathology. These molecules induce changes in cerebral endothelial cells leading to the surface expression of adhesion molecules, such as ICAM-1, CD36, and thrombospondin-related protein, and parasite adhesion (6, 7). However, IFNγ and TNFα have also been reported to protect against malaria (8-10). The involvement of anti-inflammatory cytokines in malaria remains a matter of debate and several studies in humans have reported associations between high concentrations of IL-10 and either severe malaria or protection (5, 11-14).

It has recently been shown that production of autoantibodies to brain voltage-gated calcium channels, but not other ion calcium channels, increased with severity of *P. falciparum* infection in Kenyan children (15). Antibodies to central nervous system proteins have been associated with seizure and epilepsies in several autoimmune diseases and are thought to play a role in the pathology (16). Hypergammaglobulinemia and polyclonal B-cell activation commonly occur in *Plasmodium* sp. infections (17-19). Some of the antibodies produced recognize self-components from various tissues and organs, such as erythrocytes, lymphocytes, nucleic acid structures, cytoskeleton, smooth muscle, heart and thyroid (20-28). Evidence is accumulating that high levels of antibodies against phospholipid (PL), cardiolipin (CL), ssDNA, dsDNA, and rheumatoid factor are correlated with disease severity in *P. falciparum*-infected patients (22, 25, 29-31), and Coombs' anti-globulin test is positive in *P. falciparum*-infected individuals suffering from severe anemia (32-35). It is unclear whether self-reactive antibodies play a role in protective immunity against blood-stage parasites (36-38). Moreover, it is not known whether the presence of these autoantibodies is a consequence of the infection or whether it contributes to the events leading to severe malaria, including the development of neurological complications linked to *P. falciparum* cerebral malaria. In addition, it remains unclear whether IFNγ, TNFα and IL-10 regulate the self-reactive antibody response during malaria. Self-reactive antibody response in primary biliary cirrhosis (39) is regulated by the three cytokines mentioned above.

In that context, the inventors have investigated several parameters, amongst which the presence of autoantibodies directed against brain tissues in *P. falciparum* malaria, in order to identify relevant markers for diagnosing cerebral malaria. To that aim, and as described in detail in the experimental part below, they recruited three groups of patients attending the Owendo Pediatric Hospital and Libreville Hospital Center in Gabon according to their clinical status at admission: uncomplicated malaria (UM), severe non-cerebral malaria (SNCM) or cerebral malaria (CM). Using sera collected from these patients, they combined a quantitative immunoblot (PANAMA-blot) method facilitating the comparison of thousands of antigens simultaneously (40, 41) with multivariate analyses to compare the repertoire of IgG reactivities to human brain antigens developed in the sera of controls and *P. falciparum*-infected patient groups. They further investigated whether levels of circulating TNFα, IFNγ and IL-10 in these groups of patients were associated with the repertoire of IgG reactivities and disease phenotype.

The inventors have demonstrated the presence of high level of autoantibodies largely directed against the α chain of non-erythroid spectrin (also called fodrin) in *P. falciparum* malaria. The results disclosed in the experimental part below show that there is a relationship between the autoantibody level and the clinical symptoms, and that self-reactive antibodies are associated to the development of cerebral malaria, especially when associated with high circulating TNFα concentration. More specifically, the inventors have demonstrated that the self-reactive antibodies present at a high level in cerebral malaria patients are predominantly directed against the central and/or the C-terminal parts of the α chain of non-erythroid spectrin. In what follows, the "central part of the α chain of non-erythroid spectrin" is defined as the part of the protein spanning from approximately the amino acid 1139 to the amino acid 1498, and the "C-terminal part of the α chain of non-erythroid spectrin" encompasses the residues 1499 to 2472 of the protein.

Besides, non-erythroid spectrin is released in the cerebrospinal fluid of patients suffering from severe brain injury, such as cerebral malaria.

The present invention hence pertains to the use of antibodies specific for the α chain of non-erythroid spectrin, as a prognostic and/or diagnostic marker of cerebral malaria. Antibodies specific for the central part and/or the C-terminal part of the α chain of non-erythroid spectrin, for example antibodies which recognize an epitope present on a polypeptide selected amongst the polypeptides of SEQ ID Nos: 45 and 14-29 described below, will preferably be used according to the present invention. These markers are the first seric markers described for prognosticating and/or diagnosing cerebral malaria.

The α chain of non-erythroid spectrin or spectrin breakdown products can also be detected in the cerebrospinal fluid of patients suffering from cerebral malaria, taking advantage of the fact that the cerebrospinal fluid is systematically collected in malaria patients with in a coma state, for the diagnosis of meningitis. These degradation products are polypeptidic fragments of the α chain of non-erythroid spectrin. In particular, fragments comprising antigenic sequences such as those of SEQ ID Nos: 1 to 29 and 45 and more specifically, those selected amongst SEQ ID No: 45 and SEQ ID Nos: 14 to 29, can be sought, for example through an immunoassay, for prognosticating and/or diagnosing cerebral malaria.

The present invention also concerns a method for in vitro prognosticating and/or diagnosing cerebral malaria, which comprises a step of detecting non-erythroid spectrin or fragments thereof, and/or antibodies directed against non-erythroid spectrin, in a biological sample.

Non-erythroid spectrin is a major component of the cytoskeleton of most eukaryotic cells. It forms heterodimers composed of α and β subunits. Erythroid spectrin is expressed in erythrocytes. Importantly, the alpha chain of erythroid spectrin is very different from the alpha chain of non-erythroid spectrin found in the brain. Hence, in a preferred embodiment of the above method, the level of antibodies directed against the α chain of non-erythroid spectrin is measured. According to a more preferred embodiment, the level of antibodies directed against the central part and/or the C-terminal part of the α chain of non-erythroid spectrin is measured. In the method according to the present invention, a high level of auto-antibodies specifically recognizing non-erythroid spectrin, especially its central and/or C-terminal part, is indicative of cerebral malaria.

A preferred embodiment of the present method further comprises a step of measuring the concentration of TNFα in a biological sample. Indeed, the inventors found that plasma TNFα concentrations are clearly higher in patients developing severe malaria than in those developing uncomplicated malaria. TNFα is known for mediating inflammation during CM. Furthermore, as shown in the experiment part below, the inventors observed that the CM patients with the highest TNFα plasma concentrations (>100 pg/ml) presented the highest level of reactivity with brain antigens. The level of anti-fodrin antibodies and the TNFα concentration in the serum can hence advantageously be combined to obtain a score for efficiently establishing a prognosis and/or an early diagnosis of cerebral malaria.

The antibodies which are detected in the method according to the invention are preferably G immunoglobulins (IgG).

The skilled artisan can choose any known technique to perform the above-described method. In particular, the antibodies directed against the α chain of non-erythroid spectrin can be detected and/or quantitated by performing any kind of immunoassay, such as, for example, an enzyme-linked immunosorbent assay (ELISA), a flow cytometry immunoassay or an immunochromatographic assay.

An example of ELISA-type immunoassay that can advantageously be used to perform the invention is the Bio-Plex system (Bio-Rad). This system enables multiplexing of theoretically up to 100 different assays within a single sample. Each assay is performed on the surface of a 5.5 μm polystyrene bead. The beads are filled with different ratios of two different fluorescent dyes, resulting in an array of 100 distinct spectral addresses. Each set of beads can be conjugated with a different capture molecule. For example, each bead with a specific fluorescence is conjugated with a specific antigenic peptide. The conjugated beads can then be mixed and incubated with the sample in a microplate well to react with specific antibodies. Captured antibodies, specific for determined epitopes, can then be simultaneously quantitated by flow cytometry.

In a preferred embodiment, the methods disclosed herein are adapted to be run with a limited instrumentation, and in conditions which are not optimal for the conservation of reagents. For these reasons, immunochromatographic assays, such as lateral flow test strip or dipstick, can advantageously be used to perform the present methods.

One or several molecules can be used as capture molecules in the immunoassays for performing the above methods. Among those, the following can be cited: the whole non-erythroid spectrin, the α chain of non-erythroid spectrin and fragments thereof, as well as antigenic molecules derived from the α chain of non-erythroid spectrin. By "antigenic molecules derived from the α chain of non-erythroid spectrin" is meant an antigenic fragment of the α chain of the fodrin, but also any kind of molecule presenting an epitope of said antigen, such as an optimized polypeptide retaining the epitope sequence but having some mutations in the residues adjacent to said epitope, provided the epitope presentation is retained.

The capture molecules used according to the invention are preferably specific for the α chain of non-erythroid spectrin. Examples of antigenic molecules which are specific for the α chain of non-erythroid spectrin are the polypeptides of SEQ ID Nos: 1 to 29, disclosed in Table 1 below. Of these, SEQ ID No: 45 and SEQ ID Nos: 14 to 20 from the central part of the protein, and SEQ ID Nos: 15 to 29 are from its C-terminal part. Examples of antigenic molecules which cross react with antibodies directed against both erythroid and non-erythroid spectrins are the polypeptides of SEQ ID Nos: 30 to 44, disclosed in Table 2 below.

TABLE 1 examples of antigenic peptides specific for the α chain of non-erythroid spectrin. The numbers indicate the N and C-terminal positions of the peptides in the α chain of non-erythroid spectrin.

| SEQ ID No | SEQUENCE |
|---|---|
| 1 | 56-LEKWIQEKLQIASDENYKDP-75 |
| 2 | 94-ANSGAIVKLDETGNLMISEGHFASETI-120 |
| 3 | 195-TDMAAHEERVNEVNQFAAKLIQEQHPEEELIKTKQD-231 |
| 4 | 276-QLMASDDFGRDLASVQALLRKHEGL-300 |
| 5 | 318-ADRLQQSHPLSATQIQVKREELITN-342 |
| 6 | 416-SFKSADESGQALLAAGHYAS-435 |

TABLE 1-continued examples of antigenic peptides specific for the α chain of non-erythroid spectrin. The numbers indicate the N and C-terminal positions of the peptides in the α chain of non-erythroid spectrin.

| SEQ ID No | SEQUENCE |
|---|---|
| 7 | 436-NNHYAMEDVATRRDALLSR-454 |
| 8 | 597-TDEAYKDPSNLQGKVQKHQAFEA-619 |
| 9 | 635-G QKLIDVNHYAKDEVAARMNEVISLWKKLLEA-666 |
| 10 | 688-EDIELWLYEVEGHLASDDYGKDLTNVQNLQKKHALLEADVAAH-730 |
| 11 | 747-AGHFDAENIKKKQEALVARY-766 |
| 12 | 1053-TRITKEAGSVSLRMKQVEELYHSLLE-1078 |
| 13 | 1087-LEKSCKKFMLFREANELQQWINEKEAALTSEEVGADLEQVEVLQ-1130 |
| 45 | 1151-NKVAEDLESEGLMAEEVQAVQQQEXYGMMPRDETDSKTASPWKSARLM-1198 |
| 14 | 1160-EGLMAEEVQAVQQQEXY-1176 |
| 15 | 1177-GMMPRDETDSKTASPWKSARLMVHTVATFNSI-1208 |
| 16 | 1160-EGLMAEEVQAVQQQEXYGMMPRDETD-1195 |
| 17 | 1196-SKTASPWKSARLMVHTVATFNSI |
| 18 | 1386-TEIDARAGTFQAFEQFGQQLLAHGHYASP-1414 |
| 19 | 1468-NTEDKGDSLDSVEALIK-1484 |
| 20 | 1478-SVEALIKKHEDFDKAINVQEE-1499 |
| 21 | 1453-CEQAENWMAAREAFLNTEDKGDSLD-1477 |
| 22 | 1500-KIAALQAFADQLIAAGHYAK-1519 |
| 23 | 1617-IERGACAGSEDAVKARLAALADQWQFLVQK-1646 |
| 24 | 1671-DFWLSEVEALLASEDYGKDLASVN-1694 |
| 25 | 1939-KNNHHEENISSKMKGLNGKVSDLEK-1963 |
| 26 | 2000-KTDDYGRDLSSVQTLLT-2016 |
| 27 | 2038-ALKDQLLAAKHVQSK-2052 |
| 28 | 2114-LTDPVRCNSL-2123 |
| 29 | 2456-LPTAFDYVEFTRSLFVN-2472 |

TABLE 2 examples of antigenic peptides from the α chain of non-erythroid spectrin. The numbers indicate the N and C-terminal positions of the peptides in the α chain of non-erythroid spectrin.

| SEQ ID No | SEQUENCE |
|---|---|
| 30 | 239-RLKGLALQRQ-248 |
| 31 | 390-LASDVAGAEALLDR-420 |
| 32 | 462-QYEQCMDLQLFY-473 |
| 33 | 857-AAEDVKAKLHE-867 |
| 34 | 925-AEALLKKH-931 |
| 35 | 1149-DINKVAE-1155 |
| 36 | 1225-RSQLLGSAHEVQR-1237 |
| 37 | 1262-GHDLASVQALQ-1272 |
| 38 | 1280-RDLAALGDKVNS-1291 |
| 39 | 1440-MLDQCLELQLFHRD-1453 |
| 40 | 1687-GKDLASVNNLLKKHQLLEADI-1707 |
| 41 | 1809-LEAELAAHEPAIQGVLDT-1826 |

TABLE 2-continued examples of antigenic peptides from the α chain of non-erythroid spectrin. The numbers indicate the N and C-terminal positions of the peptides in the α chain of non-erythroid spectrin.

| SEQ ID No | SEQUENCE |
|---|---|
| 42 | 1841-IQQRLAQFVEH-1851 |
| 43 | 1983-WKADVVES-1990 |
| 44 | 2275-ALILDN-2280 |

In a preferred embodiment of the method according to the invention, at least one of the antigenic molecules used as capture molecules is selected in the group consisting of the polypeptides of SEQ ID Nos: 1 to 29 and 45. In a more preferred embodiment, at least one of the antigenic molecules used as capture molecules is selected in the group consisting of the polypeptides of SEQ ID Nos: 45 and 14 to 29. In another embodiment, at least one additional antigenic molecule is selected in the group consisting of the polypeptides of SEQ ID Nos: 30 to 44. In these embodiments, each capture molecule can advantageously be conjugated to a labelled bead (or microparticle, nanoparticle and the like), so that a multiplex immunoassay (for example, a multiplex ELISA-type assay) can be performed on a single sample. The present invention hence also pertains to the use of a polypeptide selected amongst the polypeptides of SEQ ID Nos: 1 to 29 and 45, and/or amongst the polypeptides of SEQ ID Nos: 30 to 44, possibly conjugated to a labelled particle, in an immunoassay aimed at prognosticating and/or diagnosing cerebral malaria.

Alternatively, the method according to the invention can be performed by performing an immunocapture assay as described in Example 8 below, in which an anti-human immunoglobulin antibody is used as a capture molecule, and a labelled non-erythroid spectrin or fragment thereof is used for the detection of the antibodies directed against the α chain of non-erythroid spectrin. In a particularly advantageous embodiment, this kind of immunocapture assay is adapted to be performed in an immunochromatographic assay, such as a lateral flow test strip or a dipstick.

According to another embodiment of the invention, the method for in vitro prognosticating and/or diagnosing cerebral malaria comprises a step of detecting the non-erythroid spectrin itself, or fragments thereof, in a biological sample. In this embodiment, polyclonal or monoclonal antibodies directed against non-erythroid spectrin are advantageously used for detecting said non-erythroid spectrin or fragment thereof. For example, monoclonal antibodies directed against a polypeptide selected amongst the polypeptides of SEQ ID Nos: 1 to 29 and 45, preferably amongst the polypeptides of SEQ ID Nos: 45 and 14 to 29, can be obtained and used to that aim.

The methods of the invention can be performed on different kinds of biological samples, such as, for example, blood, plasma or cerebrospinal fluid. Cerebrospinal fluid will be used for the detection of non-erythroid spectrin or fragment thereof, whereas blood or plasma are preferably used for detection of seric markers such as antibodies and degradation fragments of the non-erythroid spectrin.

The present invention also pertains to a kit for establishing a prognosis and/or a diagnosis of cerebral malaria, which comprises at least one antigenic molecule derived from the α chain of non-erythroid spectrin. In preferred kits, at least one antigenic molecule is selected in the group consisting of the α chain of non-erythroid spectrin and its fragments of SEQ ID Nos: 1 to 45. Even more preferably, the kit comprises at least one antigenic molecule comprising an epitope which is present on the α chain of non-erythroid spectrin but not on erythroid spectrin, such as, for example, the polypeptides of SEQ ID Nos: 45 and 1 to 29. According to a particularly preferred embodiment of such a kit, at least one antigenic molecule comprised in the kit is selected amongst the polypeptides of SEQ ID Nos: 45 and 14 to 29.

In a preferred embodiment of the kit according to the invention, at least one antigenic molecule is bound to a support such as, for example a labelled particle. By "labelled particle" is meant any kind of bead, microbead, nanoparticle, semiconductor nanocrystal and the like.

Alternatively, at least one antigenic molecule is labelled, and the kit according to the invention further comprises an antibody directed against human antibodies, which is preferably monoclonal, and which can be bound to a support such as, for example, a microplate, a microbead, or a membrane.

As mentioned above, the skilled artisan will preferably choose, as materials and reagents to be included in the kit, components that will be easy to use without the need for heavy laboratory infrastructures.

The kit according to the invention can also comprise, in place of the antigens or in addition thereto, monoclonal or polyclonal antibodies directed against the α chain and/or the β chain non-erythroid spectrin.

The invention is further illustrated by the following figures and examples.

FIGURE LEGENDS

FIG. 1: Day 0 plasma cytokine concentrations. A. TNFα; B. IL-10. Horizontal bars in all panels indicate groupwise median values. UI: uninfected control, UM: uncomplicated malaria, SNCM: severe non cerebral malaria, CM: cerebral malaria.

FIGS. 1A-1B: Day 0 plasma cytokine concentrations. FIG. 1A. TNFα; FIG. 1B. IL-10. Horizontal bars in all panels indicate groupwise median values. UI: uninfected control, UM: uncomplicated malaria, SNCM: severe non cerebral malaria, CM: cerebral malaria.

Figure 2:
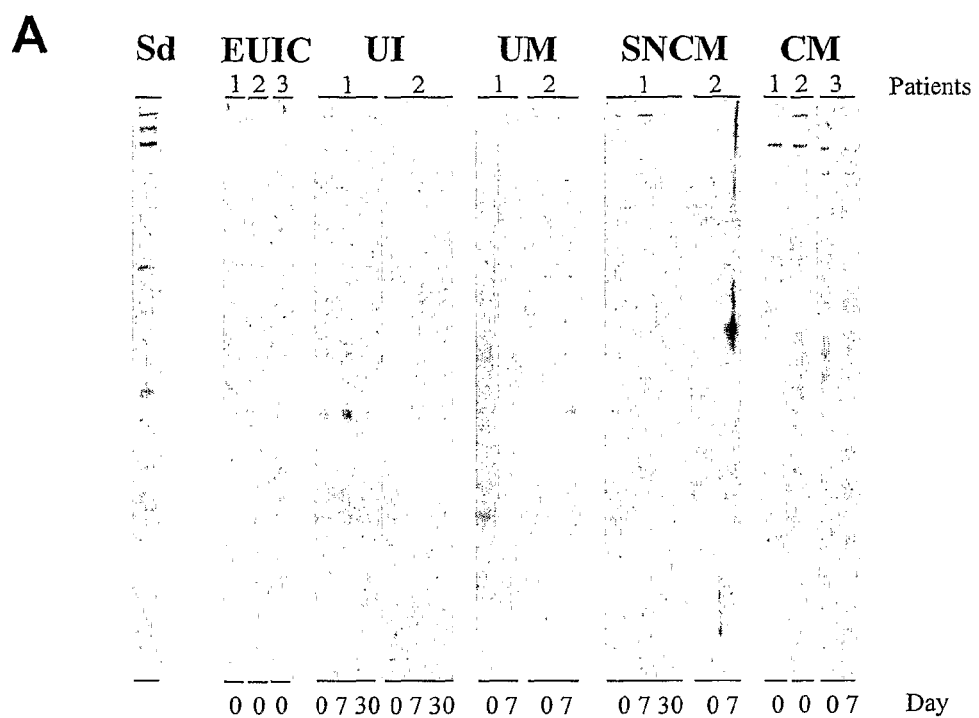
Figure 2:
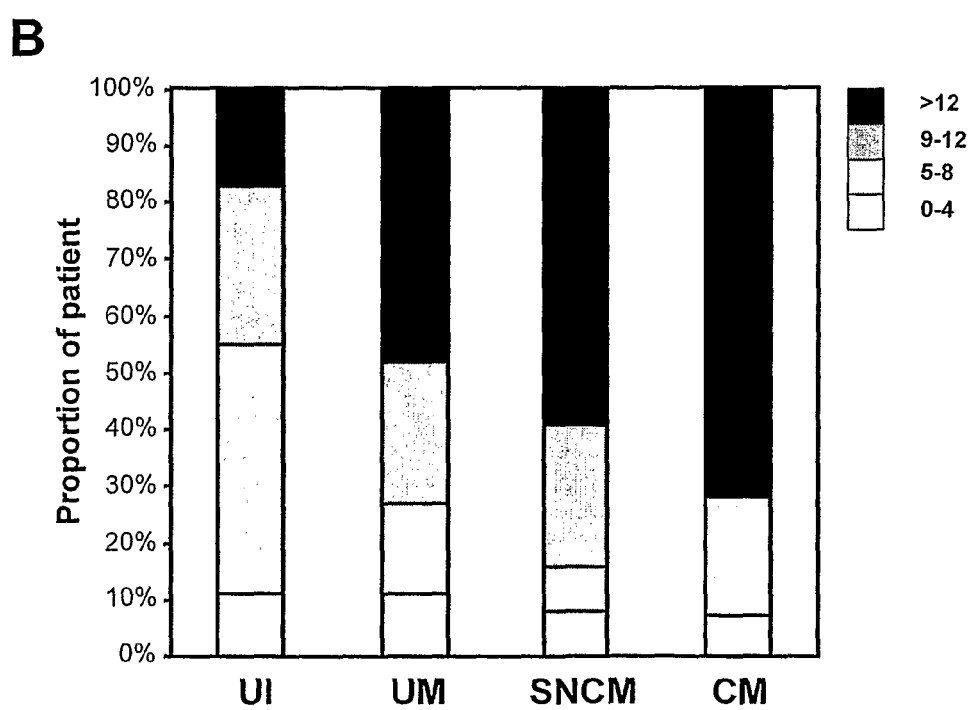

FIGS. 2A-2B: FIG. 2A. IgG immunoreactivity profiles for 2, 2, 2, 2 and 3 patients in the EUIC, UI, UM, SNCM and CM groups, respectively at day 0, day 7 and day 30 for each patient. FIG. 2B. Frequency of patients in each group recognizing ranges of 0-4, 5-8, 9-12 and more than 12 bands, respectively. Sd: standard plasma, EUIC: European uninfected control, UI: uninfected control, UM: uncomplicated malaria, SNCM: severe non cerebral malaria, CM: cerebral malaria.

Figure 3:
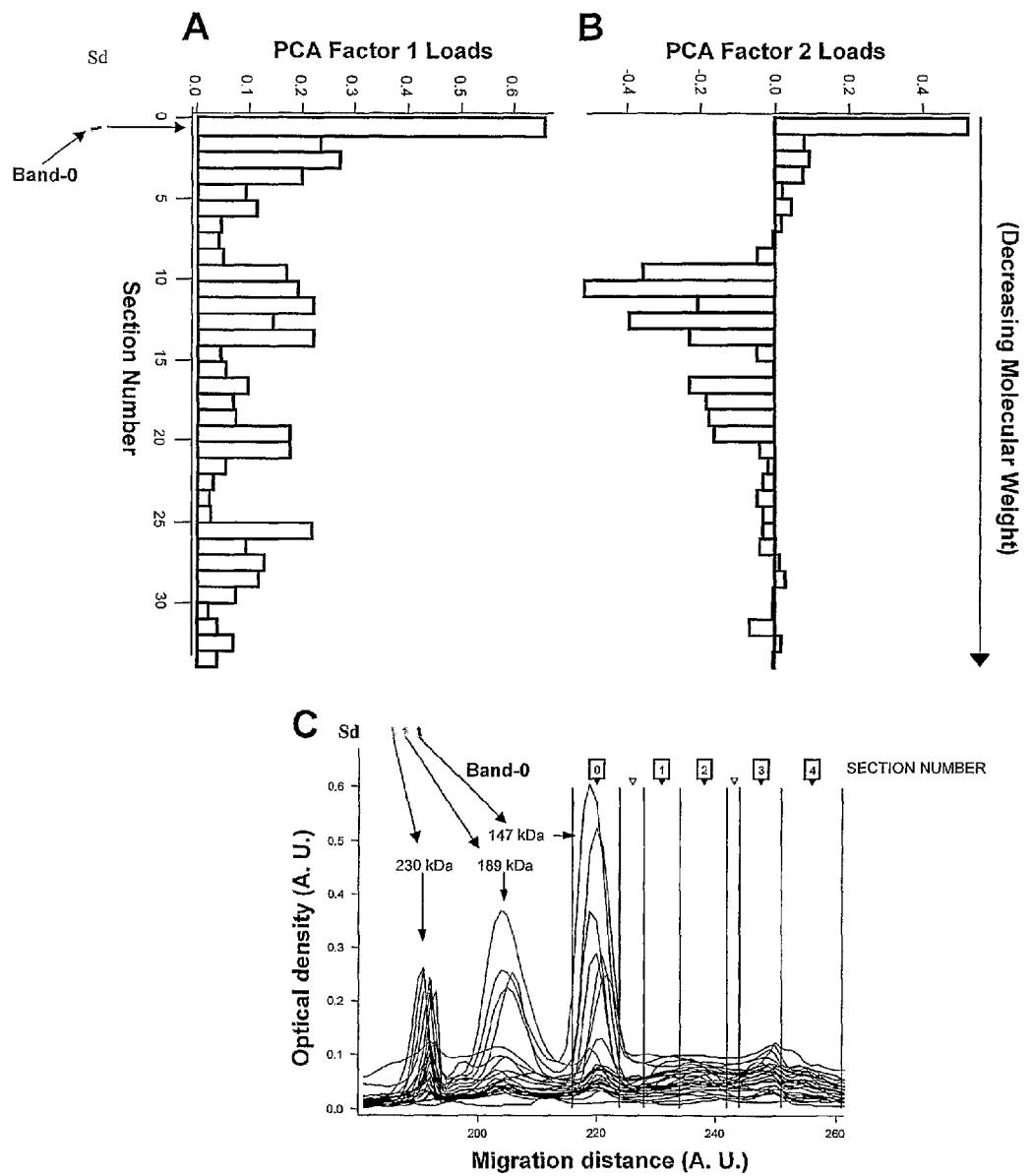

FIGS. 3A-3C: PCA factor loads: Relative contributions of reactivity bands to the first two PCA factors calculated on unadjusted profiles of IgG immunoreactivity to brain proteins separated by 10% SDS-PAGE. FIG. 3A. PCA factor 1. FIG. 3B. PCA factor 2. FIG. 3C. localisation of the band 0 on Western blot profile obtain after the computer analysis of membran N° 5. Bands are ordered from high to low molecular weight (between about 230 kDa and 20 kDa). PCA: Principal component analysis. Sd: standard plasma.

Figure 4:
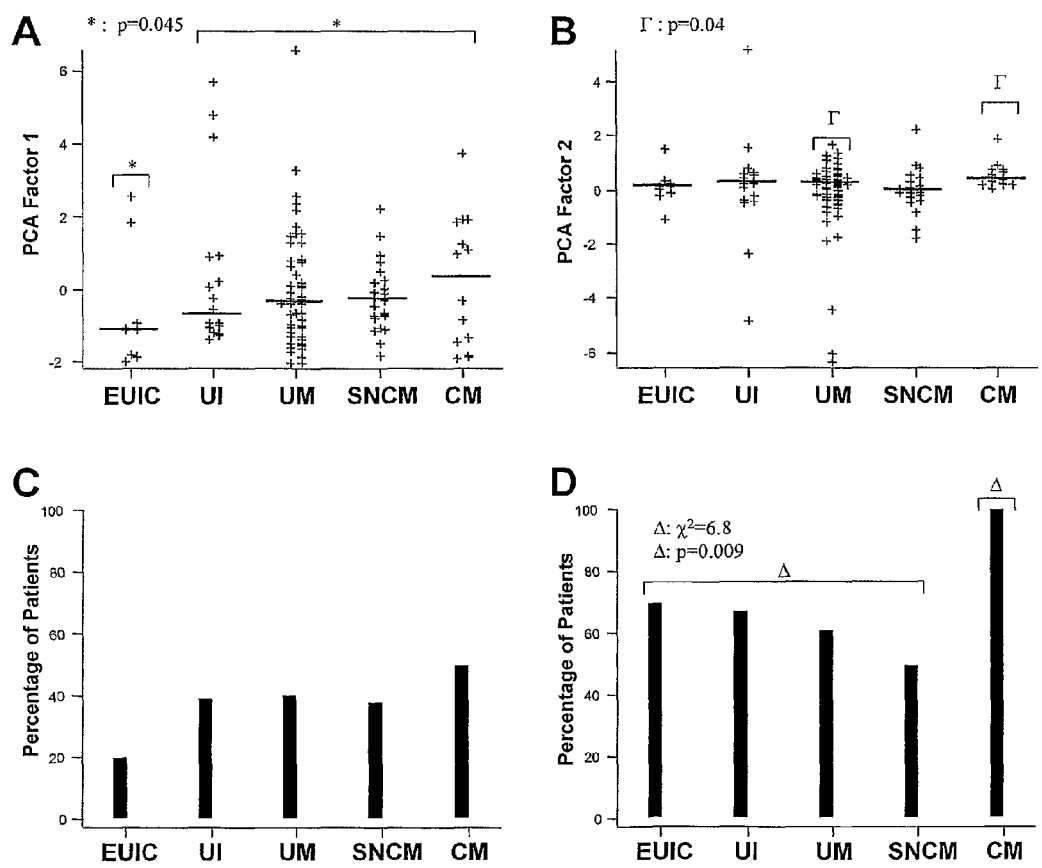

FIGS. 4A-4D: PCA factor scores from unadjusted IgG immunoreactivity profiles. FIG. 4A. Groupwise distribution of factor 1 scores. FIG. 4B. Groupwise distribution of factor 2 scores. FIG. 4C. Frequency of patients in each group with above-average factor 1 scores. FIG. 4D. Frequency of patients in each group with above-average factor 2 scores. EUIC: European uninfected control, UI: uninfected control, UM: uncomplicated malaria, SNCM: severe non cerebral malaria, CM: cerebral malaria.

Figure 5:
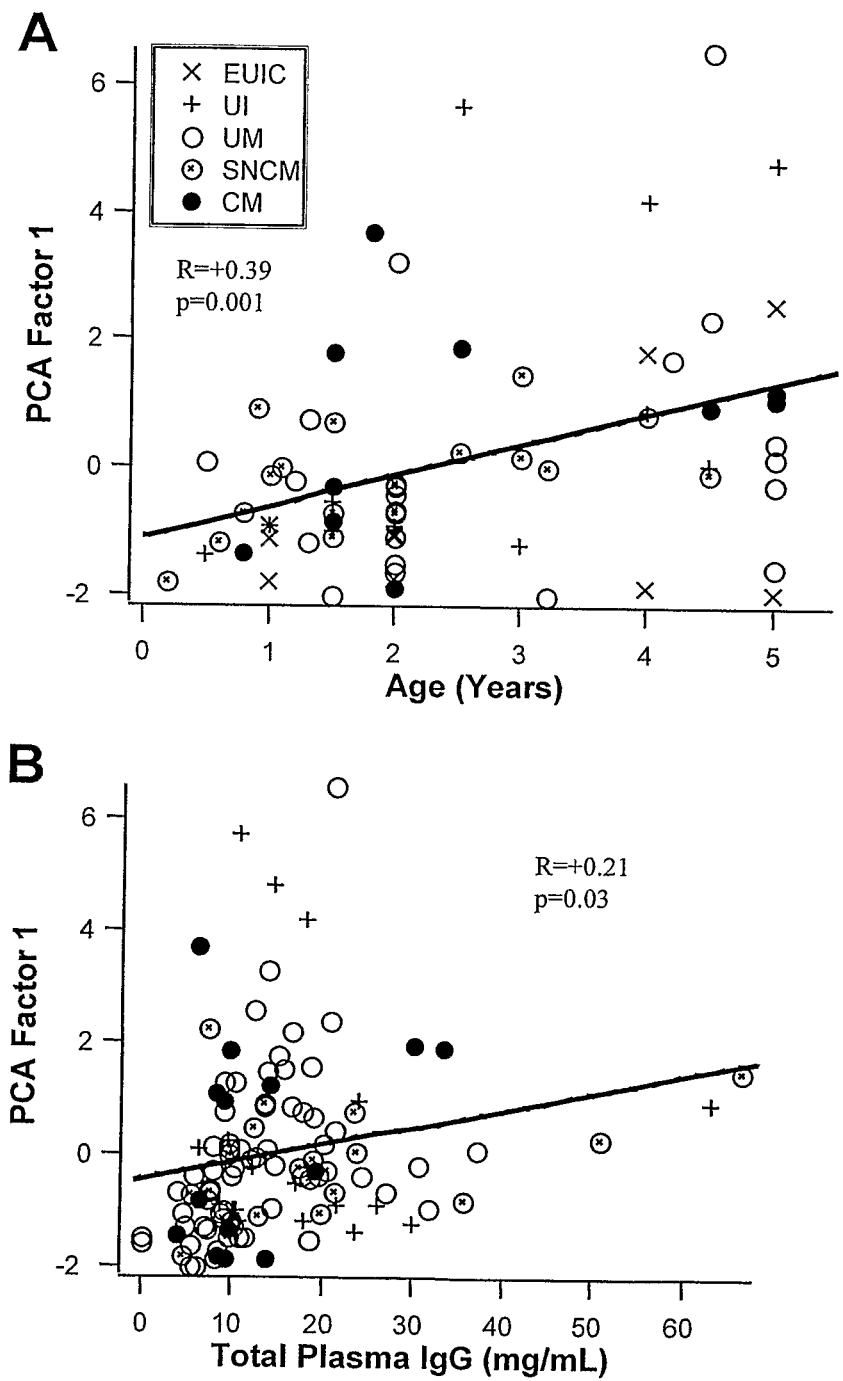

FIGS. 5A-5B: Properties of unadjusted IgG anti-brain reactivity in terms of PCA factor 1 scores. FIG. 5A. Association with age. FIG. 5B. Association with total plasma IgG concentration. Regression lines in both panels are calculated on all patients. EUIC: European uninfected control, UI: uninfected control, UM: uncomplicated malaria, SNCM: severe non cerebral malaria, CM: cerebral malaria.

Figure 6:
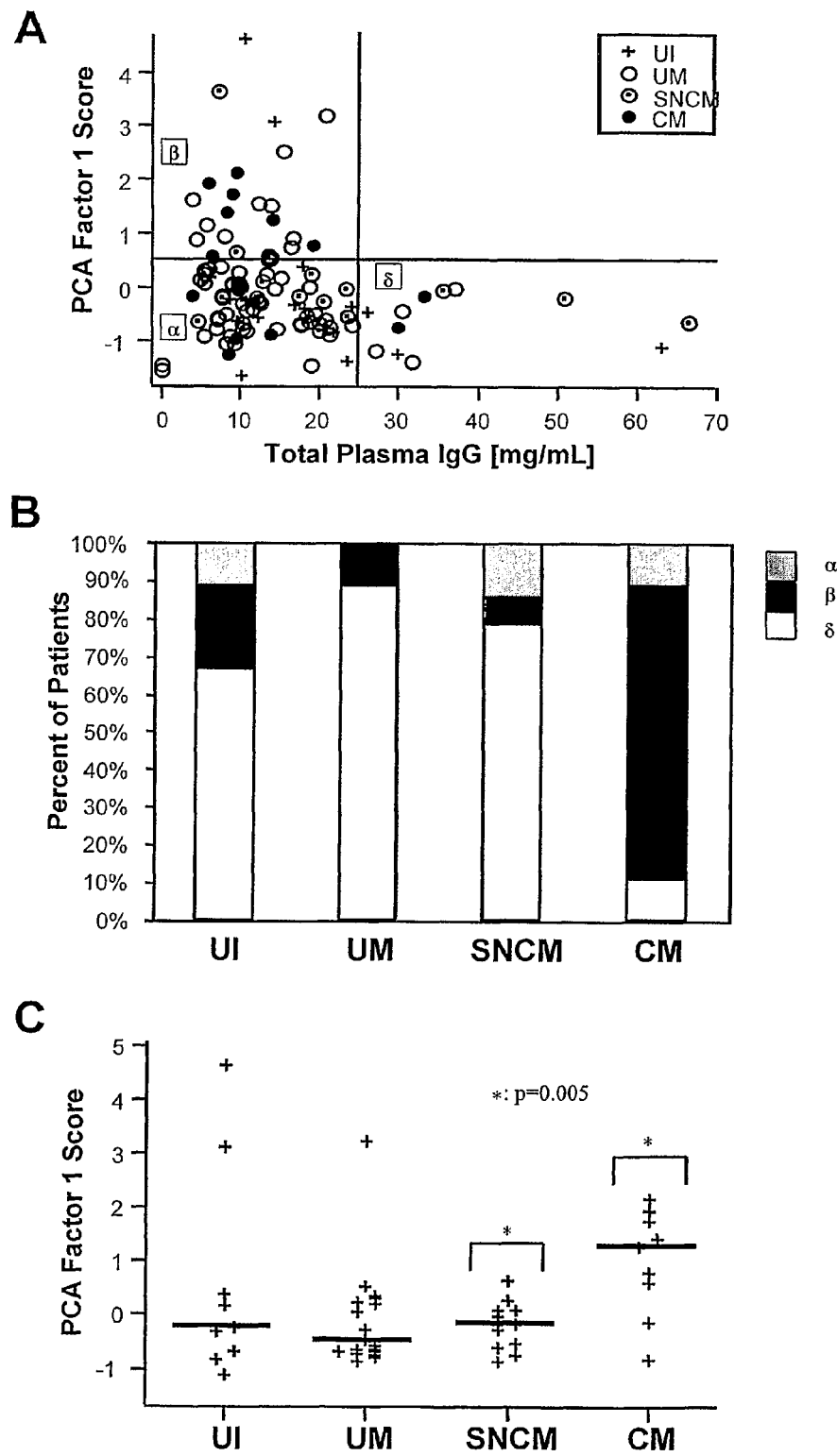

FIGS. 6A-6C: Properties of adjusted IgG anti-brain reactivity in terms of PCA factor 1 scores. FIG. 6A. Relationship to total plasma IgG concentration, and dissection into three subgroups: α (IgG<25 mg/ml; F1<0.5), β (IgG<25 mg/ml; F1>0.5), δ (IgG>25 mg/ml; F1<0.5). FIG. 6B. Frequencies of patients above one year of age in each group, over the three subgroups. FIG. 6C. Groupwise distribution of PCA factor-1 scores among patients older than one year, with horizontal bars indicating median values. The significance of the difference between patients with cerebral malaria (CM) and with noncerebral clinical malaria (UM+SNCM) is indicated. UI: uninfected control, UM: uncomplicated malaria, SNCM: severe non cerebral malaria, CM: cerebral malaria.

Figure 7:
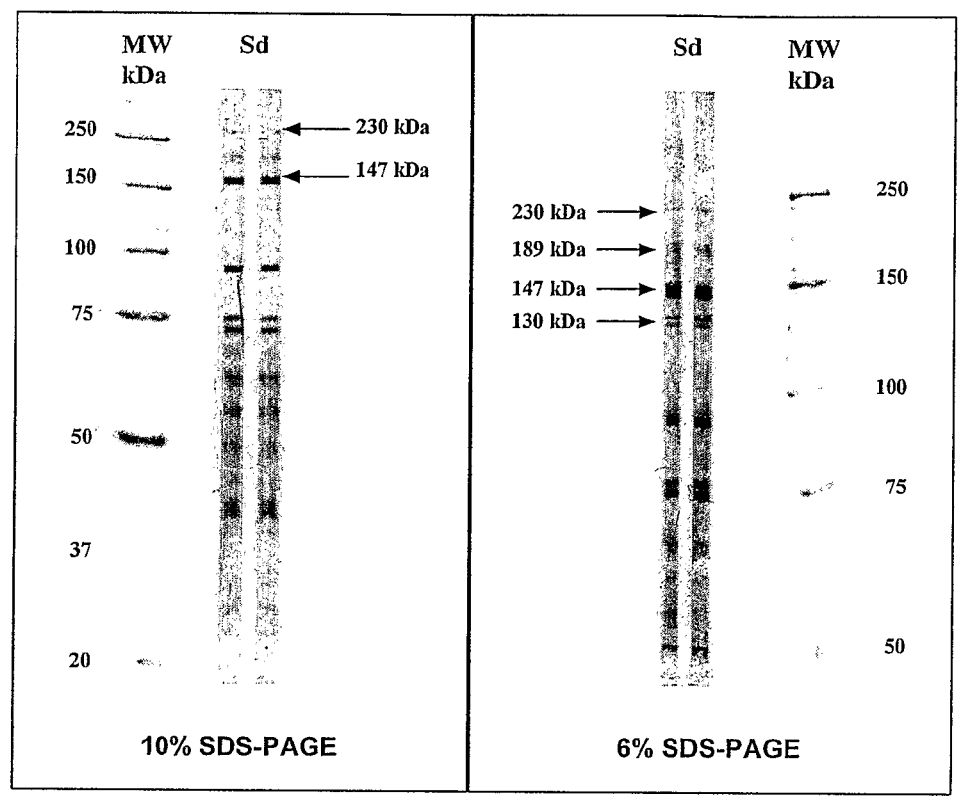

FIG. 7: IgG immunoreactivities to brain proteins separated by 10% (left) and 6% (right) SDS-PAGE. For three bands corresponding to high-molecular weight proteins, molecular weights have been estimated by comparison with markers. Sd:standard plasma. KDa:kilo Dalton. MW:molecular weight.

Figure 8:
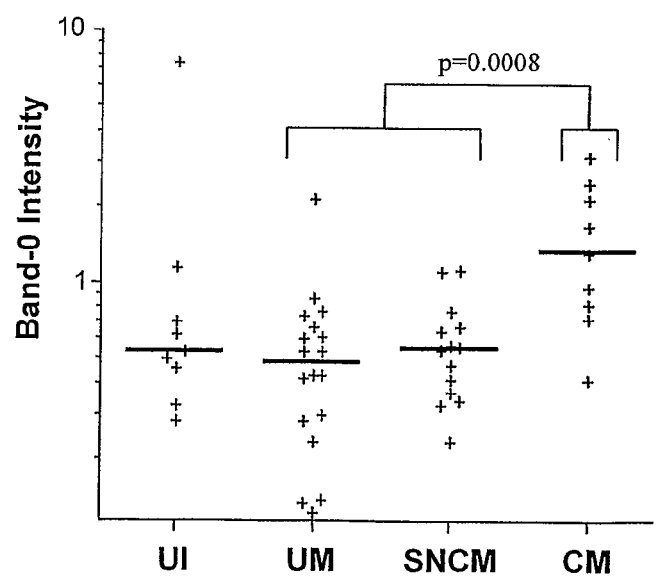

FIG. 8: Intensity of IgG reacting to band 0 in children older than one year in each group. Horizontal bars indicate medians; the significant difference between patients with cerebral malaria (CM) and with noncerebral clinical malaria (UM+SNCM) is indicated. UI: uninfected control, UM: uncomplicated malaria, SNCM: severe non cerebral malaria, CM: cerebral malaria.

Figure 9:
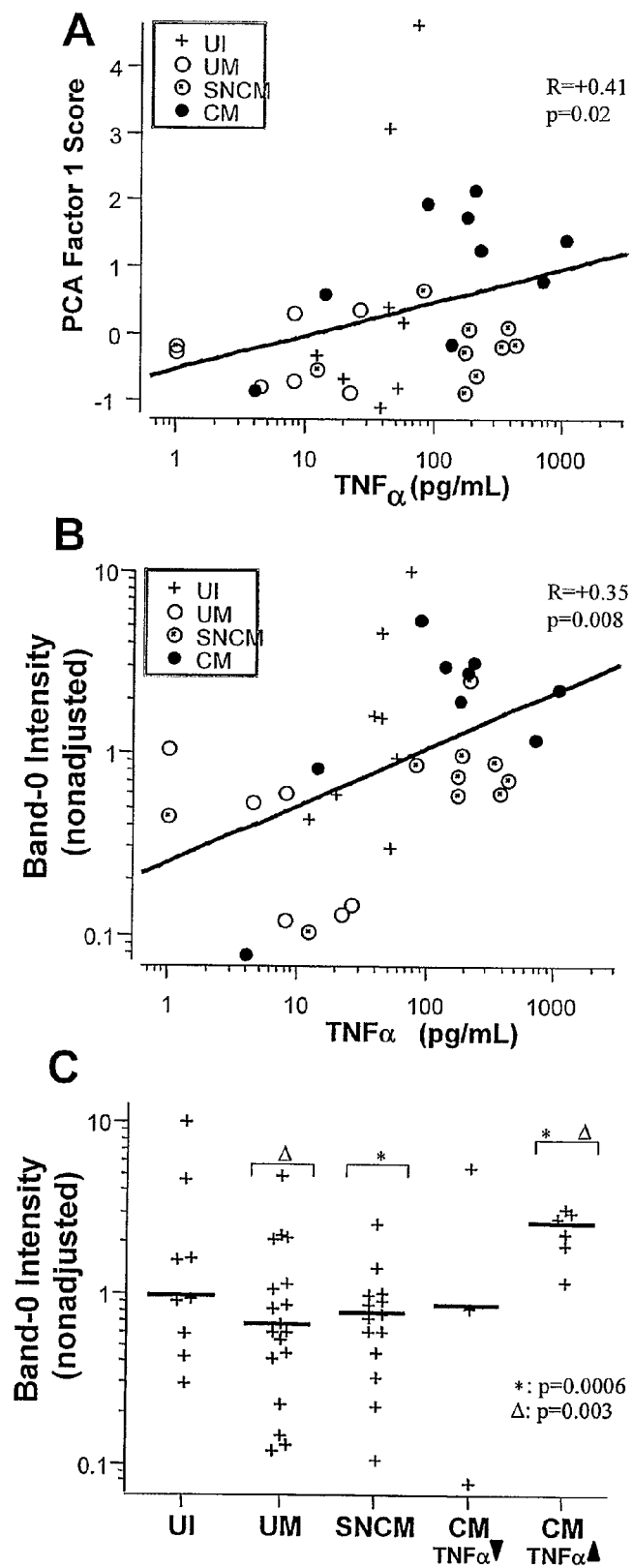

FIGS. 9A-9C: Total reactivity to brain proteins and intensity of IgG reacting to band 0 as a function of plasma cytokine levels in children older than 1 year. FIG. 9A. Positive correlation between PCA factor 1 and TNFα concentrations in the CM group, indicated by dashed regression line. FIG. 9B. Positive correlation between unadjusted reactivity to band 0 and TNFα levels. FIG. 9C. High band 0 reactivity was observed most frequently in CM patients with TNFα levels above 100 pg/mL (indicated as high-TNFα in a separate group on the right). Horizontal bars indicate medians. Only children over the age of 1 year are shown. UI: uninfected control, UM: uncomplicated malaria, SNCM: severe non cerebral malaria, CM: cerebral malaria.

Figure 10:
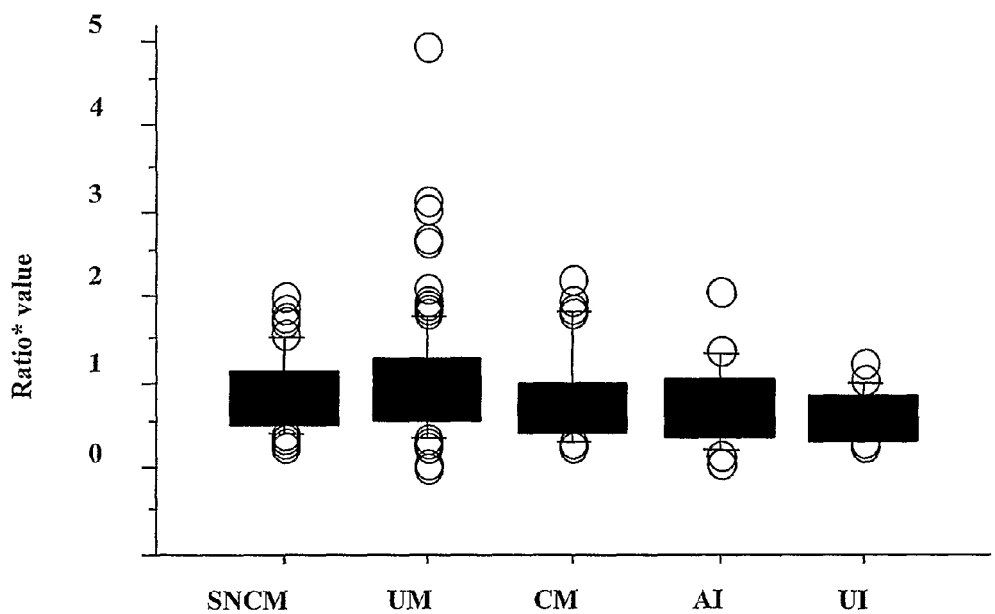

FIG. 10: Anti-IgG erythrocyte spectrin ELISA result. Box plot representation of the ratio for individuals by groups. AI: asymptomatic infected individuals; CM: cerebral malaria; SNCM: severe non-cerebral malaria; UI: uninfected individuals; UM: uncomplicated malaria. * Ratio is defined as follow: (OD sample—OD background)/(OD positive control–OD background).  Positive control is a pool of patients included in each ELISA plate.

Figure 11:
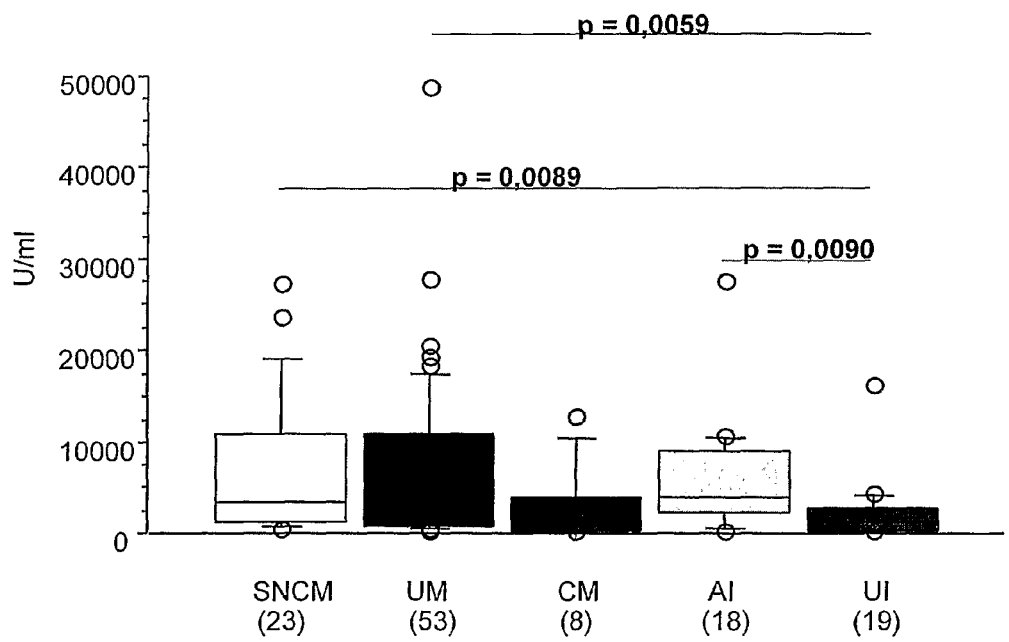

FIG. 11: Concentration of IgGs anti-N-terminal fragment of the α chain of the non erythroid spectrin. The number of individuals tested is indicated under the name of the corresponding group. Bar charts represent the median values. The extreme values are represented by open circles. The statistical analysis was realized using the non parametric Kruskal-Wallis test followed by a non parametric Mann-Whitney (Statview 5.0, Institute Inc., Cary, N.C.).

EXAMPLES

Abbreviations

Throughout these examples, the following abbreviations will be used: EUIC, European uninfected controls; UI, uninfected; UM, uncomplicated malaria; SNCM, severe non-cerebral malaria; CM, cerebral malaria; TNFα, tumor necrosis factor alpha; IFNγ, interferon gamma; IL-10, interleukin-10; PL, phospholipid; CL, cardiolipin; PCA, principal component analysis; OPH, Owendo Pediatric Hospital; LHC, Libreville Hospital Center; OPD, Ophenylenediamine; SDS, sodium dodecyl sulfate; Sd, Standard plasma; DTT, dithiothreitol; TLCK, N-α-tosyl-L-lysine chloromethyl ketone.

Patients and Methods

The following examples were performed using samples from patients and methods as described below.

Study Population

Patients were included in the study only after informed consent had been obtained from their parents, at the Owendo Pediatric Hospital (OPH) and Libreville Hospital Center (LHC) in Gabon, between 1996 and 2000. The ethics committee of the Gabon Health Office approved this study. Patients were assigned to the various groups on the basis of World Health Organization guidelines for the definition of uncomplicated and severe malaria. The children included in this study were aged between 2 months and 5 years, and fell into three groups for *P. falciparum* malaria: 1) uncomplicated malaria (UM), 2) severe non-cerebral malaria (SNCM) with severe anemia (hemoglobin level<5 g/dl) or hypoglycemia (glycemia<2.2 mmol/ml), and 3) cerebral malaria (CM) with a Blantyre Coma Score<2, or three convulsive episodes during the 24 hours before admission, with a post-critical comatose stated lasting >15 minutes. A control group was also studied—the uninfected group (UI)—comprising children with *P. falciparum*-negative thin blood smears. All patients presenting diseases other than malaria were excluded from the study. All the UI subjects (25) were from the same area of Libreville City, and the patients in the UM (66), SNCM (36) and CM (21) groups were all recruited from the OPH and LHC hospitals (Table 3). During the recruitment period, 5.4% (8/148) of the patients died in CM group. There was no significant difference in mean age between the children in the various groups, with the exception of the SNCM group, for which the mean age was lower. No significant differences in sex ratio were observed, with a 1:1 ratio of boys to girls in every group (Table 3).

TABLE 3

Distribution of patients according to age and sex in different groups.

| Staff | | UI | UM | SNCM | CM | Total |
|---|---|---|---|---|---|---|
| | | 25 | 66 | 36 | 21 | 148 |
| Age | Mean | 2.9 | 3.2 | 1.8 | 2.7 | 2.6 |
| | Range | (0.5-5) | (0.5-5) | (0.2-4.5) | (0.5-5) | (0.2-5) |
| Sex | Male | 13 | 23 | 18 | 13 | 67 |
| | Female | 11 | 32 | 14 | 8 | 65 |
| Mortality | | 0 | 0 | 0 | 8 | 8 (5.4%) |

UI controls were examined daily for clinical symptoms. Parasitemia (thin blood smears) was determined on days 0, 7 and 30. UI subjects were checked for intestinal helminthiasis on days 0 and 30. Each individual received 400 mg of oral albendazole (Zentel®) on day 7. Patients were treated with amodiaquine or quinine, depending on disease severity. Children with uncomplicated malaria were given oral amodiaquine (25 mg/kg) for three days; those with severe malaria received intravenous quinine (25 mg/kg/day) for five days. Children with severe anemia underwent blood transfusion. None of the participants had suffered from CM before.

Blood Sample Collection

Venous blood from each patient was collected into EDTA in sterile vacutainers on the day of hospitalization (day 0, before any treatment), day 7 and day 30. Plasma was obtained by centrifuging blood samples at 5000 g for 15 min. Plasma samples were stored at −80° C. until use.

Parasite Assessment

Parasitemia was assessed by counting asexual forms of *P. falciparum* on thin blood smears under a light microscope after staining with 10% Giemsa solution. One thousand red blood cells were scored and parasitemia is expressed as the percentage of infected red blood cells.

Antibodies

Total IgG were quantified by "sandwich type" ELISA using a mouse monoclonal anti-human IgG (γ-chain specific) unconjugate (Sigma Aldrich, France) for plates coating and a secondary goat polyclonal peroxidase-conjugated anti-human IgG (γ-chain specific) (Sigma Aldrich, France). The standard was done using total purified human IgG (Immunopure, human IgG, whole molecule, Pierce, France). Immunoblot was performed using a secondary goat polyclonal anti-human IgG (γ-chain specific) conjugated to the Alkaline Phosphatase (Sigma Aldrich, France).

Quantification of Total Plasma IgG

For quantification of the IgG in the patients' plasma, 96-microwell plates (Reacti-Bind 96 EIA Plat. Corn. Not. 100/PING, Pierce) were coated by incubation overnight at 4° C. with 5 μg/ml of monoclonal anti-human IgG antibodies (Sigma-Aldrich, France). Plates were washed with 0.05% Tween in PBS and saturated by incubation with 1% gelatin in PBS for 1 hour at 37° C. Plasma samples were then serially diluted in 1% gelatin and 0.01% Tween-20 in PBS. 100 μl of diluted plasma were added to each coated well and incubated the plates for 2 hours at 37° C. The plates were washed thoroughly and incubated with peroxidase-conjugated anti-human IgG for 2 hrs at 37° C. Binding was detected in the dark, using 100 μl/well O-phenylenediamine (OPD) in 0.05 Mphosphate-citrate buffer, pH5 (Sigma-Aldrich, France) as the substrate. The peroxidase reaction was stopped after 30 min by adding 10% SDS (sodium dodecyl sulfate). Absorbance was measured at 450 nm, with an ELISA plate reader. The total amount of IgG in the sample was determined from a standard curve covering the range 0.001-2 μg/ml IgG. Each sample was tested in duplicate.

Cytokine Assays

A sandwich-type ELISA was used to determine cytokine levels (TNFα, IFNγ and IL-10), using a kit (OptEIA set, Pharmingen, BD Bioscience, France), according to the manufacturer's recommendations. Cytokine levels were determined in blood samples from 106 patients chosen at random from the various groups (18 UI, 26 UM, 25 SNCM and 20 CM). The amounts of TNFα, IFNγ and IL-10 in the samples were calculated from standard curves covering the range 1.1 to 75 pg/ml for IFNγ, 1.9 to 1000 pg/ml for IL-10 and 1.9 to 2000 pg/ml for TNFα.

Brain Extract Preparation, Gel Electrophoresis and Immunoblotting

These methods were as described elsewhere (41). Briefly, normal human brain tissue from a person with no brain disease was solubilized and homogenized on ice by mechanical disruption in 60 mM Tris, 2% SDS, 100 mM DTT (dithiothreitol), 1.0 μg/ml aprotinin, 1.0 μg/ml pepstatin, 50 μg/ml TLCK (N-α-tosyl-L-lysine chloromethyl ketone), pH 6.8. Brain extract proteins were stored at −20° C. Proteins (about 300 μg protein/gel) were separated by a standard SDS-PAGE in a 10% acrylamide gel, at 25 mA. All electrophoresis reagents were purchased from Bio-Rad (Richmond, Calif.). The proteins were transferred onto nitrocellulose membranes (Schleicher & Schull, Dassel, Germany) by semi-dry electrotransfer (Pasteur Institute, Paris) for 1 h at 0.8 mA/cm². Membranes were blocked by incubation overnight at room temperature with 0.2% Tween 20 in PBS (PBST).

Membranes were then incubated with patient plasma samples diluted 1:20 in PBST (non-adjusted assay), or to a total IgG concentration of 200 μg/ml (adjusted assay), in a Cassette Miniblot System (Immunetics, Cambridge, Mass.). This cassette system consists of 28 incubation channels, permitting the simultaneous incubation of each membrane with 22 individual samples and 2 standard plasma samples. Membranes were incubated for 4 hrs at room temperature with gentle shaking. They were then removed from the cassettes and bound immunoglobulins were detected by incubation with chain-specific secondary rabbit anti-human IgG coupled to alkaline phosphatase (Sigma-Aldrich) for 90 minutes at room temperature. Immunoreactivity was detected with NBT/BCPI (nitroblue tetrazolium/5-bromo-4-chloro-3-indolyl-phosphate).

The molecular weights of brain proteins were determined by comparison with "Precision Plus Protein Standards" (Bio-Rad, Richmond, Calif.) after separation by SDS-PAGE in 6% and 10% acrylamide gels. This standard contains ten highly purified recombinant proteins with molecular masses from 10 to 250 kDa.

Data Treatment and Quantification of Immunoreactivity

Dried membranes were scanned with a high resolution scanner (600 DPI), using an 8-bit linear grayscale as previously described (41). The proteins on the membrane were then stained with colloidal gold (Protogold, BritishBioCell, Cardiff, GB) and scanned again. The corresponding total protein staining was used in the spaces between the incubation slots to adjust immunoreactivity profiles for migration inequalities so that equivalent immunoreactivities could be re-scaled to equivalent positions on a common standard migration scale. Protein staining was also used to adjust different blots with the same cerebral extract to each other and a standard plasma sample was applied twice to the gel for total intensity adjustment. A mixture of diverse Gabonese plasma preparations diluted ½₀ was used as the standard plasma sample.

Protein Identification by Mass Spectrometry.

Protein bands localization on the gel was done by Western-blot (same experimental procedure used for the repertoire analysis) after 10% acrylamide gels SDS-PAGE separation of the brain protein extract using a pool of sera from 10 CM patients defined exhibiting a high reactivity with the band of interest. For each gel, half of the gel was used to transfer protein onto nitrocellulose membrane and western-blot analysis. The other half was stained with brilliant R250 Coomassie blue (Bio-Rad). After immunoblotting and protogold staining of the proteins on the membrane, densitometric pictures were used to adjust the protein profile and identify the protein bands. Protein bands from the half gel stained by Coomassie were selected and excised manually using a clean scalpel, and then analyzed by mass spectrometry.

Proteins were identified by peptide mass fingerprinting with a matrix-assisted laser desorption ionization-time of flight (MALDI-TOF) mass spectrometer (MS), Voyager DE-STR (Applied Biosystems, Framingham, Mass., USA). The Investigator Progest system (Genomic Solutions) was used for in gel digestion of proteins with modified porcine trypsin (Promega). The Investigator ProMS system (Genomic Solutions) was used for sample desalting (μZip-TipC18, Millipore) and for loading the sample with the matrix (α-cyano 4-hydroxy-cinnamic acid) on the MALDI sample plate. Internal calibration of MALDI spectra was carried out using the autolysis peaks of the trypsin.

For searching NCBInr database, monoisotypic masses were assigned using a local copy of Mascot (Matrix Science, London, UK). Parameters were set as follows: no restriction on the isoelectric point of proteins, a maximum mass error of 50 ppm and one incomplete cleavage per peptide was considered.

Statistical Analysis

As cytokine concentrations and parasite loads were far from normally distributed, being closer to log-normal distributions, these data were systematically described, displayed and analyzed with log-transformation. For this transformation, undetectable plasma cytokine levels were considered to be 1 pg/ml (minimal detection threshold). Linear correlation and regression analyses were also carried out on the log-transformed data for these parameters. Immunoblot data were analyzed by multivariate statistical methods, using IGOR software (Wavemetrics, LakeOswego, Oreg.), including specially written software packages. The standard migration scale was divided into sections around individual peaks of immunoreactivity. After subtraction of a baseline, peak areas under the respective densitometric profile were determined for each section and divided by the section length. Individually recognized band numbers were determined by counting sections with values above 50% of the standard plasma value when averaged over all sections. Section-wise absorbance values were subjected to principal component analysis (PCA), based on covariance calculation, a classical method for the multivariate analysis of highly dimensional correlated data involving projection onto characteristic subspaces of lower dimensionality. PCA factors are ordered according to the proportion of the total data variance fitted. Thus, the first component (Factor 1) is the one-dimensional fitting vector that accounts for the largest proportion of the variance and factor 2 is the second-best uncorrelated one-dimensional vector fitting the data. For quantitative comparisons between groups, Mann-Whitney (between two groups) or Kruskal-Wallis (>2 groups) tests were used. Qualitative association was tested by Pearson's $\chi^2$ test. The association between continuous quantitative parameters was assessed by linear regression, with the exception of correlations between two different types of parameters such as reactivity and cytokine profiles, which were tested by Spearman's rank correlation. P values<0.05 were considered significant.

Example 1

Total Plasma IgG and Cytokines Concentrations According to Age, Sex, Parasitemia and Clinical Status Parasitemia and circulating IgG levels were determined on day 0 (hospital admission) for the 129 patients randomly selected and distributed between the various groups as follows: UI (18) UM (61), SNCM (33) and CM (17) (data not shown). Median parasitemia levels did not differ significantly between the groups: UM (3.2%), SNCM (2.8%) and CM (4.0%). Parasitemia was not significantly associated with either sex or age. No significant difference in total IgG levels was observed between the UI, UM, SNCM and CM groups on day 0 (data not shown). Total IgG levels were also similar between the sexes and did not increase with parasite load. However, plasma total IgG concentration increased with age.

Plasma TNFα, IL-10 and IFNγ concentrations were determined on day 0 (before treatment) in 18 UI, 26 UM, 25 SNCM and 20 CM patients. Plasma TNFα concentrations were significantly higher in the UI, SNCM and CM groups than in the UM group (p=0.0006, p=0.0001 and p=0.001, respectively) (FIG. 1A). Plasma TNFα concentrations in patients with severe malaria (SNCM and CM) differed significantly from those in UI subjects, whereas no significant difference in these concentrations was observed between SNCM and CM patients. However, 75% of SCM patients who died had a very high plasma level of TNFα (62.5% from 500 to 1520 pg/ml, and 12.5% from 100 to 500 pg/ml) (data not shown). Plasma IL-10 concentrations were lowest in the UI group, followed by the UM group, then the CM group, and finally the SNCM group (FIG. 1B). IL-10 levels were significantly lower in the UI group than in the UM (p=0.0009) and severe malaria groups (p<0.0001), but were similar in the UM, SNCM and CM groups. Thus, unlike TNFα concentrations, IL-10 concentrations did not differ significantly between the UM, SNCM and CM groups. IL-10 was the only one of the three cytokines studied significantly associated with parasite load on day 0, both for the UM group ($R_{Spearman}$=+0.65; p=0.003), and for all infected patients ($R_{Spearman}$=+0.27; p=0.03) (data not shown). None of the cytokines determined on day 0 was significantly associated with age or sex in the sample as a whole or in any of the groups. IFNγ concentrations were highest in the UM and CM groups (data not shown). The differences between the CM and UI groups were statistically significant (p=0.007), whereas no significant differences were observed between the UM, SNCM and CM groups.

Example 2

Diversity of IgG Reactivity with Brain Antigens in the Various Clinical Groups

The patterns of recognition of brain antigens by plasma IgG from *P. falciparum*-infected patients with different clinical forms of malaria were compared. Patterns were detected by quantitative immunoblotting (PANAMA-blot), using a protein extract from the brain of a healthy individual as the source of antigens. An adjusted assay was carried out as previously described (40-42), in which patient plasma was systematically diluted for testing at an identical total IgG concentration (200 μg/ml), to determine the proportion of total IgG accounted for autoantibodies. 122 of the patients enrolled were randomly selected in the cohorts, and analyzed sera collected on day 0 (hospital admission), day 7 and day 30. It was not possible to determine the profiles of nine patients due to precipitation. The remaining patients were distributed as follows: 18 UI, 57 UM, 24 SNCM, and 14 CM. FIG. 2A-2B shows typical examples of the immune profiles obtained with the brain extract, for several patients of each group, on days 0, 7 and 30. Reactivity patterns were more diverse in the UM, SNCM and CM groups than in the UI and EUIC (European uninfected controls) group, but did not change over this time period (FIG. 2A). The median number of cerebral antigens recognized by plasma IgG was significantly higher in UM (p=0.02), SNCM (p=0.01) and CM (p=0.02) than in UI (data not shown) subjects, whereas the difference in the number of bands recognized did not differ significantly between UM, SNCM and CM patients. The proportion of patients in each group with plasma IgG recognizing a particular number of bands (FIG. 2B) was determined. The proportion of individuals with a large number of bands (>12) was higher in CM (71%) and SNCM (58%) than in UM (49%) and UI (17%) subjects. The overall difference between groups was significant ($\chi^2$=11.2, p=0.01). Thus, the number of brain antigens recognized by circulating IgG from *P. falciparum*-infected individuals increased with disease severity, with the sera of most UI subjects reacting with less than eight bands (FIG. 2B).

Example 3

Relationship Between Size of the IgG Repertoire Directed Against Brain Antigens and Disease Severity The distribution of circulating IgG reactivities to brain proteins was investigated by carrying out a second quantitative immunoblot assay, using the same method but analyzing every plasma sample at a fixed dilution of 1/20 (non-adjusted assay). Ten European children of similar ages who had never been exposed to malaria were included in this assay. The patterns of reactivity of the patients were then analyzed by principal component analysis (PCA), fitted to the Gabonese data. In PCA, the components are identified in decreasing order of importance. Thus, by definition, the first two components identified account for a large proportion of total reactivity. Factor 1 was characterized by overall positive factor loads (FIG. 3A-3C). Factor 1 scores therefore provide a quantitative measure of total reactivity. Factor 2 scores mostly reflected the recognition of one particular section (the section-0) rather than the others. Factor 1 and factor 2 scores were higher in CM than in UI, UM and SNCM patients (FIG. 4A-4B). Factor 1 scores were significantly lower in EUIC than in Gabonese UI (p=0.045). No significant difference was observed between the UI, UM, SNCM and CM groups (FIG. 4A). Factor 2 scores differed significantly between CM and SNCM patients (p=0.001) and between CM and UM patients (p=0.04) (FIG. 4B).

The proportion of patients with high factor 1 scores (and therefore high overall anti-brain reactivity) appeared to be highest for CM patients, but no significant difference was found between the groups (FIG. 4C). The proportion of patients with high factor 2 scores was significantly lower in EUIC, UI, UM and SNCM (70%, 67%, 61%, and 50%, respectively) than in CM (100%) subjects (Yates-corrected $\chi^2$=6.8, p=0.009; $\chi^2_{All\ Groups}$=10.4, p=0.03) (FIG. 4D). Remarkably, all CM patients had factor 2 scores above the mean.

In addition to the day 0 samples, samples taken from the same individuals (14 UI, 42 UM, 27 SNCM and 3 CM patients) on days 7 and 30 after admission were also analyzed. The factor scores obtained for these samples were determined by projection, using factor loads calculated from day 0 data. Factor 1 scores increased significantly between days 0 and 7 in patients developing malaria whereas, on day 30, reactivity patterns were identical to those on day 7 for most of the children (data not shown). No such increase was observed in factor 2 scores.

Example 4

Reactivity to Brain Proteins According to Age, Sex, Parasitemia and Circulating IgG Levels The reactivity to brain antigens represented by factor 1 scores was significantly correlated with age (R=+0.39, p=0.001) (FIG. 5A) in the non-adjusted assay, whereas no correlation was found between reactivity profiles, sex and parasitemia (data not shown). However, circulating IgG concentration was found to be significantly correlated with reactivity in all groups (R=+0.21, p=0.03) (FIG. 5B) except for uninfected controls (data not shown). These correlations with total IgG concentration and age were less significant (p=0.038 and 0.026, respectively) if adjusted immunoblot assays were used for PCA analyses. Thus, determining proportions, as for the assessment of diversity, may better reflect intrinsic repertoire properties and make it possible to address specific changes. In the adjusted assay, high anti-brain reactivity (factor 1 scores) was observed only for patients with low total IgG concentrations (FIG. 6A). Children were assigned to three subgroups, as follows: α) low anti-brain reactivity and moderate levels of circulating IgG (below 25 mg/dl), β) high anti-brain reactivity and moderate levels of circulating IgG and δ) low anti-brain reactivity and high levels of circulating IgG. Subgroups α and β displayed unequal distributions of UM, SNCM and CM patients. UM and SNCM patients were overrepresented in subgroup α (72% of the UM and 75% of the SNCM patients, but only 36% of the CM patients; χ-squared test for all groups: p=0.049). Subgroup β included 50% of the CM patients but only 21% of all samples (χ-squared test: p=0.028). No preferential distribution of any particular group of patients was observed in subgroup δ.

During the first twelve months of life, the plasma may contain maternal IgG. The differences between the three subgroups were more pronounced if the analysis was limited to factor 1 scores for the adjusted anti-brain reactivity of sera from children over the age of one year. In this analysis, subgroup α contained 89% of the UM and 79% of the SNCM patients but only 11% of the CM patients, whereas 78% of CM patients were found in subgroup β (FIG. 6B). The association between the levels of brain-reactive IgG and clinical status was highly significant for subgroups α and β (p=0.0005 and 0.0004, respectively). Similarly, CM patients over the age of one year also showed the highest anti-brain reactivity (factor 1 scores) (FIG. 6C). Factor 1 scores were significantly higher for CM than for SNCM and UM patients (p=0.005 and 0.009, respectively) in the adjusted assay.

Thus, IgG reactivity against the brain, which was correlated with both age and total plasma IgG concentration in the unadjusted assay, reflects non-specific differences in the natural autoantibody repertoire. Conversely, the results for the adjusted assay, in which the effect of both age and total IgG concentrations was largely eliminated, indicate that a specific self-reactive antibody repertoire is induced during *P. falciparum* infection.

Example 5

IgG Reactivity to a High-Molecular Weight Brain Antigen is Associated with CM

Profiles of the reactivity of standard and patient plasma samples with brain proteins were separated into 33 sections on the standardized migration scale. PCA analysis revealed that reactivity with section 0, corresponding to a set of high-molecular weight proteins, was the most informative (FIG. 3A-3C). In the two types of assay, this section had the most impact on PCA factor 1. For PCA factor 2, section 0 was distinguished from the rest of the repertoire by a positive load. Section 0 includes at least three proteins with estimated molecular weights of 230 kDa, 147 kDa and a double band at 130 kDa on SDS-PAGE in a 6% acrylamide gel with protein size standards (FIG. 7). In adjusted assays, plasma IgG from children with CM over the age of one year reacted more strongly with the brain proteins contained in section 0 than did plasma IgG from children of the UM and SNCM groups (both p=0.0008) (FIG. 8): 90% of the CM patients had a detectable reaction, versus 50% SNCM 44% UI and 39% UM patients (data not shown). The results obtained in unadjusted assays were qualitatively similar, but the differences between CM and UM and between CM and SNCM were less significant (p=0.02 and 0.01, respectively). Unadjusted reactivity with section 0 proteins increased with age (R=0.25; p=0.04) (Data not shown).

Example 6

Mass Spectrometry Identification

Proteins from human brain extract were separated on a 10% acrylamide gel. After Coomassie staining, three bands corresponding to reactive bands detected by Western blot were cut and their protein contents analyzed by peptide mass fingerprinting. In three independent experiments, band 1 corresponded to the beta chain of the non-erythroid spectrin isoform 2 while bands 2 and 3 to seven different isoforms of the alpha chain of the non-erythroid spectrin. In this latter case, it is not possible to distinguish if only one, several or all these isoforms are present in bands 2 and 3 (Table 4).

TABLE 4

Mass fingerprinting results.

| Band number | | NCBI accession number | MW (kDa) | Matching peptides | Sequence coverage (%) | Mascot score* |
|---|---|---|---|---|---|---|
| band 1 | | gi\|30315658 | 251 | 28 | 15 | 89 |
| band 2 | and/or | gi\|56757656 | 285 | 64 | 28 | 401 |
| | | gi\|55663122 | 285 | 64 | 28 | 401 |
| | | gi\|31565122 | 282 | 64 | 28 | 400 |
| | | gi\|62089306 | 288 | 64 | 28 | 399 |
| | | gi\|55663121 | 288 | 64 | 28 | 398 |
| | | gi\|1805280 | 285 | 64 | 28 | 398 |
| | | gi\|4507191 | 284 | 63 | 28 | 390 |
| band 3 | and/or | gi\|56757656 | 285 | 53 | 24 | 303 |
| | | gi\|55663122 | 285 | 53 | 24 | 303 |
| | | gi\|31565122 | 282 | 53 | 24 | 303 |
| | | gi\|62089306 | 288 | 53 | 24 | 300 |
| | | gi\|55663121 | 288 | 53 | 24 | 300 |
| | | gi\|1805280 | 285 | 53 | 24 | 300 |
| | | gi\|4507191 | 284 | 53 | 24 | 303 |

*Mascot score is 10XLog(p), where p is the probability that the observed match is a random event. Protein scores greater than 64 are significant ($p < 0.05$).

Example 7

Relationships Between IgG Reactivity to Brain Proteins, Plasma Cytokine Profile and Clinical Manifestations of Malaria The inventors assessed whether IgG autoantibody response and the type of disease were associated with a specific circulating cytokine profile in *P. falciparum*-infected patients. Plasma IFNγ concentrations and reactivity were not associated in the various groups. In the adjusted assay, reactivity to brain antigens, as measured by PCA factor 1 score, was positively correlated with TNFα concentration. This correlation was significant for children over the age of one year ($R_{Spearman}$=+0.41, p=0.02) (FIG. 9A). Factor 1 score was particularly high in the CM patients with the highest plasma TNFα concentrations (>100 pg/ml). The intensity of the unadjusted (but not of the adjusted) reactivity with the section 0 band was also correlated with TNFα concentrations (in all children: $R_{Spearman}$=+0.35, p=0.008; children aged over 1 year: $R_{Spearman}$=+0.54, p=0.002) (FIG. 9B). Reactivity with section 0 bands was significantly stronger for the CM patients with the highest plasma TNFα concentrations (>100 pg/ml) than for SNCM and UM patients (p=0.0006 and p=0.003, respectively) (FIG. 9C).

Example 8

Immunocapture Assays

Immunocapture assays are performed to detect either IgG, IgM or IgA autoantibodies against non erythroid spectrin.

Solid phase, (microplates, microbeads, membranes) are sensitized with an anti-gamma, anti-alpha or and anti-mu human antibody (preferably monoclonal).

After an incubation period (24 h at 48° C.), the solid phase is washed and saturated.

Each sample to be tested is appropriately diluted (about 1/100 for adult serum, and about 1/10 for neonatal and infantile serum) and deposited onto the sensitized solid phase (triplicates). The solid phase is then incubated.

After washing, a labelled non erythrocyte spectrin or a fragment thereof is added onto the solid phase. The solid phase is again incubated.

After a second washing, the immune reaction is read, directly if the non erythrocyte spectrin or a fragment is itself directly labelled (magnetic or coloured particles) or indirectly if the label is an enzymatic one, by addition of the appropriate substrate and chromogen.

This assay allows the detection of slight antibody concentrations.

Example 9

Comparison of the Antibody Responses to the a Chain of the Erythroid and the Non-Erythroid Spectrin in *P. falciparum* Infected Patients The non-erythroid alpha-spectrin shares 60% of amino acid sequences identity with the human red blood cell protein (43). As autoantibodies recognizing red blood cells are frequently reported during *Plasmodium* infection, the inventors have investigated whether the self-reactive antibodies recognizing the α chain of the non-erythroid spectrin observed in CM patients are a result of a cross reactivity with the erythroid α spectrin. To this aim, they estimated plasma IgG levels against the erythroid form of this protein in the cohort of patients studied using an ELISA test. In addition to the first cohort, other individuals, including a new group defined as asymptomatic infected individuals (AI), were tested.

Anti-spectrin IgG antibodies were quantified in the plasma of the *P. falciparum* infected children. An ELISA assay was developed to test specific IgG reactivity against the erythrocyte form of the spectrin. Purified erythroid spectrin from Sigma was coated on 96 well plate at the concentration of 2.5 microg/mL. Plasma samples were tested at the dilution of 1/50 and incubated 1 hour at 37° C. Specific anti-human IgG peroxidase conjugate secondary antibody (Sigma) was incubated at the dilution of 1/500 for 1 hour at 37° C. Reactivities were revealed with OPD in citrate buffer and then stopped with 10% SDS. Optical density (OD) was quantified at 450 nm. The results were expressed as a ratio defined as (OD sample−OD background)/(OD positive control−OD background), wherein the OD positive control is a pool of plasma that was included in each plate as a positive control. Groups of patients were compared using the non parametric Mann-Whitney U-test.

Higher level of IgG reacting with erythroid spectrin was found in UM (mean of the ratio per group±standard deviation: 1.016±0.679) when compared to SNCM (0.874±0.433), CM (0.788±0.526), AI (0.752±0.484) and UI (0.643±0.285) (FIG. 10). As shown by Mann-Whitney U-tests, groups were significantly different when comparing UM vs. UI (p=0.0095), UM vs. CM (p=0.0118), CM vs. non-cerebral malaria (SNCM and UM) (p=0.015), healthy (AI+UI) vs. not healthy (UM+SNCM+CM) (p=0.0205) and infected (AI+UM+SNCM+CM) vs. not infected (UI) (p=0.0457).

These results suggest that, contrarily to what could have been expected, the antibodies against the α chain of the non-erythroid spectrin produced in CM patients and the antibodies against the α chain of the erythroid spectrin found in the plasma of the same group of malaria patients do not recognize the same epitopes. Hence, the self-reactive antibodies recognizing the α chain of the non-erythroid spectrin observed in CM patients do not result from a cross reactivity with the erythroid α spectrin.

Example 10

Self-Reactive Antibodies Produced in CM Patients are not Directed to the N-Terminal Fragment of the α Chain of the Non-Erythroid Spectrin The α chain of the non-erythroid spectrin (α-II spectrin) is cleaved during apoptosis. The cleavage is effected following activation of a neutral calcium activated protease, calpain and caspase-3, both members of cysteine protease family, which have been shown to play an important role in the proteolytic cascades associated with several other central nervous system disorders such as stroke, hypoxiaischemia, experimental hydrocephalus and spinal cord injury. Calpain mediated cleavage of intact spectrin (280 kDa) results in fragments of 150 kDa (C-terminal) and 145 kDa (N-terminal), specific for calpain.

Interestingly, antibodies against alpha-fodrin have been shown to be present in up to 98% of untreated patients with Sjögren's syndrome. These antibodies are specifically directed against an apoptotic cleavage product of alpha-fodrin, which is a 120 kDa N-terminal fragment of the α-II spectrin (product of a partial degradation of the 145 kDa-fragment mentioned above).

The inventors have investigated whether the antibodies found in Sjögren's disease patients recognized the same part of the α-II spectrin as the antibodies found in CM patients. To this aim, they used a commercial Kit (Aesku Diagnostic, Germany), which allows to quantify specific IgG to the 120 kDa N-terminal fragment of the α-II spectrin. The same cohort of patients as above was tested. The obtained data showed that the quantity of specific IgGs recognizing this N-terminal fragment of the α-II spectrin is significantly increased in the asymptomatic (AI), acute (UM) and severe non cerebral malaria (SNCM) patients by comparison with the not infected individuals living in the same endemic area (UI). To the contrary, the amount of IgGs recognizing the 120 kDa N-terminal fragment of the α-II spectrin in cerebral malaria patients (CM) was statistically the same as in uninfected subjects (UI) (FIG. 11).

In conclusion, circulating IgGs against the 120 kDa N-terminal fragment of the α-II spectrin observed in the sera of *P. falciparum* infected patients cannot explain the reactivity of circulating IgG with the α chain of the non-erythroid spectrin found in CM patients. These results also suggest that antibodies produced in AI, UM and SNCM subjects do not recognize the same antigenic peptides of the α-II spectrin as antibodies produced in CM patients. Clearly, the hypothesis of a role played by autoantibodies to brain proteins in CM pathophysiology is in agreement with the inventor's observations and with those previously made for numerous autoimmune diseases involving the brain such as multiple sclerosis. According to this concept, high levels of α-II spectrin autoantibodies found in CM patients would not be caused by the direct antigenic stimulation of anti-brain α-II spectrin lymphocytes clones, but would be a consequence of a *P. falciparum*-induced defect or weakening of the natural regulation of homunculus autoreactivity. Consequently and since the fragment of α-II spectrin recognized by the IgGs of *P. falciparum* infected patients differs from the one recognized by IgGs of CM patients, it is proposed to use the antibody to α-II spectrin as a marker of CM.

REFERENCES

1. Breman, J. G., A. Egan, and G. T. Keusch. 2001. The intolerable burden of malaria: a new look at the numbers. *Am J Trop Med. Hyg.* 64:iv-vii.
2. Idro, R., N. E. Jenkins, and C. R. Newton. 2005. Pathogenesis, clinical features, and neurological outcome of cerebral malaria. *Lancet Neurol.* 4:827-840.
3. Idro, R., G. Otieno, S. White, A. Kahindi, G. Fegan, S. Mithwani, K. Maitland, B. G. Neville, B. Ogutu, and C. R. Newton. 2005. Decorticate, decerebrate and opisthotonic posturing and seizures in Kenyan children with cerebral malaria. *Malar J.* 4:57.
4. Akanmori, B. D., J. A. Kurtzhals, B. Q. Goka, V. Adabayeri, M. F. Ofori, F. K. Nkrumah, C. Behr, and L. Hviid. 2000. Distinct patterns of cytokine regulation in discrete clinical forms of *Plasmodium falciparum* malaria. *Eur Cytokine Netw.* 11:113-118.
5. Issifou, S., E. Mavoungou, S. Borrmann, M. K. Bouyou-Akotet, P. B. Matsiegui, P. G. Kremsner, and F. Ntoumi. 2003. Severe malarial anemia associated with increased soluble Fas ligand (sFasL) concentrations in Gabonese children. *Eur Cytokine Netw.* 14:238-241.
6. Miller, K. L., P. H. Silverman, B. Kullgren, and L. J. Mahlmann. 1989. Tumor necrosis factor alpha and the anemia associated with murine malaria. *Infect Immun.* 57:1542-1546.
7. Miller, L. H., D. I. Baruch, K. Marsh, and O. K. Doumbo. 2002. The pathogenic basis of malaria. *Nature.* 415:673-679.
8. Taylor-Robinson, A. W., R. S. Phillips, A. Severn, S. Moncada, and F. Y. Liew. 1993. The role of TH1 and TH2 cells in a rodent malaria infection. *Science.* 260:1931-1934.
9. Taylor-Robinson, A. W., and M. Looker. 1998. Sensitivity of malaria parasites to nitric oxide at low oxygen tensions. *Lancet.* 351:1630.
10. Luty, A. J., B. Lell, R. Schmidt-Ott, L. G. Lehman, D. Luckner, B. Greve, P. Matousek, K. Herbich, D. Schmid, F. Migot-Nabias, P. Deloron, R. S. Nussenzweig, and P. G. Kremsner. 1999. Interferon-gamma responses are associated with resistance to reinfection with *Plasmodium falciparum* in young African children. *J Infect Dis.* 179:980-988.
11. Peyron, F., N. Burdin, P. Ringwald, J. P. Vuillez, F. Rousset, and J. Banchereau. 1994. High levels of circulating IL-10 in human malaria. *Clin Exp Immunol.* 95:300-303.

12. Ho, M., T. Schollaardt, S. Snape, S. Looareesuwan, P. Suntharasamai, and N. J. White. 1998. Endogenous interleukin-10 modulates proinflammatory response in *Plasmodium falciparum* malaria. *J Infect Dis.* 178:520-525.
13. Kurds, J. D., D. E. Lanar, M. Opollo, and P. E. Duffy. 1999. Interleukin-10 responses to liver-stage antigen 1 predict human resistance to *Plasmodium falciparum*. *Infect Immun.* 67:3424-3429.
14. Nussenblatt, V., G. Mukasa, A. Metzger, G. Ndeezi, E. Garrett, and R. D. Semba. 2001. Anemia and interleukin-10, tumor necrosis factor alpha, and erythropoietin levels among children with acute, uncomplicated *Plasmodium falciparum* malaria. *Clin Diagn Lab Immunol.* 8:1164-1170.
15. Lang, B., C. I. Newbold, G. Williams, N. Peshu, K. Marsh, and C. R. Newton. 2005. Antibodies to voltage-gated calcium channels in children with falciparum malaria. *J Infect Dis.* 191:117-121. Epub 2004 December 2001.
16. McKnight, K., Y. Jiang, Y. Hart, A. Cavey, S. Wroe, M. Blank, Y. Shoenfeld, A. Vincent, J. Palace, and B. Lang. 2005. Serum antibodies in epilepsy and seizure-associated disorders. *Neurology.* 65:1730-1736.
17. Freeman, R. R., and C. R. Parish. 1978. Polyclonal B-cell activation during rodent malarial infections. *Clin Exp Immunol.* 32:41-45.
18. Kataaha, P. K., C. A. Facer, S. M. Mortazavi-Milani, H. Stierle, and E. J. Holborow. 1984. Stimulation of autoantibody production in normal blood lymphocytes by malaria culture supernatants. *Parasite Immunol.* 6:481-492.
19. Shiddo, S. A., G. Huldt, H. Jama, L. A. Nilsson, O. Ouchterlony, M. Warsame, and J. Jonsson. 1994. Reference ranges for IgG, IgM and IgA in the serum of urban and rural Somalis. *Trop Geogr Med.* 46:27-31.
20. Houba, V., and A. C. Allison. 1966. M-antiglobulins (rheumatoid-factor-like globulins) and other gamma-globulins in relation to tropical parasitic infections. *Lancet.* 1:848-852.
21. Shaper, A. G., M. H. Kaplan, N. J. Mody, and P. A. McIntyre. 1968. Malarial antibodies and autoantibodies to heart and other tissues in the immigrant and indigenous peoples of Uganda. *Lancet.* 1:1342-1346.
22. Adu, D., D. G. Williams, I. A. Quakyi, A. Voller, Y. Anim-Addo, A. A. Bruce-Tagoe, G. D. Johnson, and E. J. Holborow. 1982. Anti-ssDNA and antinuclear antibodies in human malaria. *Clin Exp Immunol.* 49:310-316.
23. Ravindran, B., A. K. Satapathy, and M. K. Das. 1988. Naturally-occurring anti-alpha-galactosyl antibodies in human *Plasmodium falciparum* infections—a possible role for autoantibodies in malaria. *Immunol Lett.* 19:137-141.
24. Daniel-Ribeiro, C., L. Ben Slama, and M. Gentilini. 1991. Anti-nuclear and anti-smooth muscle antibodies in Caucasians, Africans and Asians with acute malaria. *J Clin Lab Immunol.* 35:109-112.
25. Jakobsen, P. H., S. D. Morris-Jones, L. Hviid, T. G. Theander, M. Hoier-Madsen, R. A. Bayoumi, and B. M. Greenwood. 1993. Anti-phospholipid antibodies in patients with *Plasmodium falciparum* malaria. *Immunology.* 79:653-657.
26. Maeno, Y., R. W. Steketee, T. Nagatake, T. Tegoshi, R. S. Desowitz, J. J. Wirima, and M. Aikawa. 1993. Immunoglobulin complex deposits in *Plasmodium falciparum*-infected placentas from Malawi and Papua New Guinea. *Am J Trop Med Hyg.* 49:574-580.
27. Wenisch, C., H. Wenisch, H. C. Bankl, M. Exner, W. Graninger, S. Looareesuwan, and H. Rumpold. 1996. Detection of anti-neutrophil cytoplasmic antibodies after acute *Plasmodium falciparum* malaria. *Clin Diagn Lab Immunol.* 3:132-134.
28. Jhaveri, K. N., K. Ghosh, D. Mohanty, B. D. Parmar, R. R. Surati, H. M. Camoens, S. H. Joshi, Y. S. Iyer, A. Desai, and S. S. Badakere. 1997. Autoantibodies, immunoglobulins, complement and circulating immune complexes in acute malaria. *Natl Med J India.* 10:5-7.
29. Soni, P. N., C. C. De Bruyn, J. Duursma, B. L. Sharp, and D. J. Pudifin. 1993. Are anticardiolipin antibodies responsible for some of the complications of severe acute *Plasmodium falciparum* malaria? *S Afr Med J.* 83:660-662.
30. Facer, C. A., and G. Agiostratidou. 1994. High levels of anti-phospholipid antibodies in uncomplicated and severe *Plasmodium falciparum* and in *P. vivax* malaria. *Clin Exp Immunol.* 95:304-309.
31. Consigny, P. H., B. Cauquelin, P. Agnamey, E. Comby, P. Brasseur, J. J. Ballet, and C. Roussilhon. 2002. High prevalence of co-factor independent anticardiolipin antibodies in malaria exposed individuals. *Clin Exp Immunol.* 127:158-164.
32. Facer, C. A. 1980. Direct antiglobulin reactions in Gambian children with *P. falciparum* malaria. III. Expression of IgG subclass determinants and genetic markers and association with anemia. *Clin Exp Immunol.* 41:81-90.
33. Ritter, K., A. Kuhlencord, R. Thomssen, and W. Bommer. 1993. Prolonged haemolytic anemia in malaria and autoantibodies against triosephosphate isomerase. *Lancet.* 342:1333-1334.
34. Stoute, J. A., A. O. Odindo, B. O. Owuor, E. K. Mibei, M. O. Opollo, and J. N. Waitumbi. 2003. Loss of red blood cell-complement regulatory proteins and increased levels of circulating immune complexes are associated with severe malarial anemia. *J Infect Dis.* 187:522-525.
35. Tones, J. R., L. Villegas, H. Perez, L. Suarez, V. M. Tones, and M. Campos. 2003. Low-grade parasitaemias and cold agglutinins in patients with hyper-reactive malarious splenomegaly and acute haemolysis. *Ann Trop Med. Parasitol.* 97:125-130.
36. Jayawardena, A. N., C. A. Janeway, Jr., and J. D. Kemp. 1979. Experimental malaria in the CBA/N mouse. *J Immunol.* 123:2532-2539.
37. Jarra, W. 1983. Protective immunity to malaria and anti-erythrocyte autoimmunity. *Ciba Found Symp.* 94:137-158.
38. Daniel-Ribeiro, C. T. 2000. Is there a role for autoimmunity in immune protection against malaria? *Mem Inst Oswaldo Cruz.* 95:199-207.
39. Krams, S. M., S. Cao, M. Hayashi, J. C. Villanueva, and O. M. Martinez. 1996. Elevations in IFN-gamma, IL-5, and IL-10 in patients with the autoimmune disease primary biliary cirrhosis: association with autoantibodies and soluble CD30. *Clin Immunol Immunopathol.* 80:311-320.
40. Nobrega, A., M. Haury, A. Grandien, E. Malanchere, A. Sundblad, and A. Coutinho. 1993. Global Analysis of Antibody Repertoires 2. Evidence For Specificity, Self-Selection and the Immunological Homunculus of Antibodies in Normal Serum. *European Journal of Immunology.* 23:2851-2859.
41. Haury, M., A. Grandien, A. Sundblad, A. Coutinho, and A. Nobrega. 1994. Global Analysis of Antibody Repertoires 1. an Immunoblot Method For the Quantitative Screening of a Large Number of Reactivities. *Scandinavian Journal of Immunology.* 39:79-87.
42. Stahl, D., S. Lacroix-Desmazes, L. Mouthon, S. V. Kaveri, and M. D. Kazatchkine. 2000. Analysis of human self-reactive antibody repertoires by quantitative immunoblotting. *Journal of Immunological Methods.* 240:1-14.
43. Baines, A. J., and J. C. Pinder. 2005. The spectrin-associated cytoskeleton in mammalian heart. *Front Biosci.* 10:3020-3033.

The invention claimed is:

1. A method for determining if a patient infected by *Plasmodium falciparum* is likely to have cerebral malaria, comprising measuring, in a blood, plasma, serum, or cerebrospinal fluid sample from said patient, a level of auto-antibodies directed against an α chain of non-erythroid spectrin, by putting said sample into contact with a fragment of the α chain of non-erythroid spectrin spanning from amino acid 1139 to amino acid 2472 of said protein, and measuring the level of auto-antibodies reacting with said fragment of the α chain of non-erythroid spectrin by immunoassay, wherein a level of auto-antibodies recognizing the α chain of non-erythroid spectrin which is higher than the level of auto-antibodies recognizing the same which is statistically observed in patients infected by *Plasmodium falciparum* but not suffering from cerebral malaria, is indicative of cerebral malaria in the patient.

2. The method according to claim 1, wherein said auto-antibodies are G immunoglobulins (IgG).

3. The method of claim 1, wherein said immunoassay is an enzyme-linked immunosorbent assay (ELISA), a flow cytometry immunoassay, an immunocapture assay, and/or an immunochromatographic assay.

4. The method of claim 1, wherein said immunoassay is an immunocapture assay, in which the auto-antibodies directed against the α chain of non-erythroid spectrin are captured by an antibody directed against human immunoglobulin, and then labelled with a labelled fragment spanning from amino acid 1139 to amino acid 2472 of non-erythroid spectrin.

5. The method according to claim 1, which further comprises a step of measuring a concentration of TNFα in a biological sample, wherein a level of TNFα which is higher than the level of TNFα which is statistically observed in patients infected by *Plasmodium falciparum* but not suffering from cerebral malaria in the patient, is indicative of cerebral malaria.

* * * * *

SEQUENCE LISTING

<160> NUMBER OF SEQ ID NOS: 45

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Glu Lys Trp Ile Gln Glu Lys Leu Gln Ile Ala Ser Asp Glu Asn
1               5                   10                  15

Tyr Lys Asp Pro
            20

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Asn Ser Gly Ala Ile Val Lys Leu Asp Glu Thr Gly Asn Leu Met
1               5                   10                  15

Ile Ser Glu Gly His Phe Ala Ser Glu Thr Ile
            20                  25

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Asp Met Ala Ala His Glu Glu Arg Val Asn Glu Val Asn Gln Phe
1               5                   10                  15

Ala Ala Lys Leu Ile Gln Glu Gln His Pro Glu Glu Glu Leu Ile Lys
            20                  25                  30

Thr Lys Gln Asp
        35

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Leu Met Ala Ser Asp Asp Phe Gly Arg Asp Leu Ala Ser Val Gln
1               5                   10                  15

Ala Leu Leu Arg Lys His Glu Gly Leu
            20                  25

<210> SEQ ID NO 5
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 5

Ala Asp Arg Leu Gln Gln Ser His Pro Leu Ser Ala Thr Gln Ile Gln
1               5                   10                  15

Val Lys Arg Glu Glu Leu Ile Thr Asn
            20                  25

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Phe Lys Ser Ala Asp Glu Ser Gly Gln Ala Leu Leu Ala Ala Gly
1               5                   10                  15

His Tyr Ala Ser
            20

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Asn His Tyr Ala Met Glu Asp Val Ala Thr Arg Arg Asp Ala Leu
1               5                   10                  15

Leu Ser Arg

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Asp Glu Ala Tyr Lys Asp Pro Ser Asn Leu Gln Gly Lys Val Gln
1               5                   10                  15

Lys His Gln Ala Phe Glu Ala
            20

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Gln Lys Leu Ile Asp Val Asn His Tyr Ala Lys Asp Glu Val Ala
1               5                   10                  15

Ala Arg Met Asn Glu Val Ile Ser Leu Trp Lys Lys Leu Leu Glu Ala
            20                  25                  30
```

```
<210> SEQ ID NO 10
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Asp Ile Glu Leu Trp Leu Tyr Glu Val Glu Gly His Leu Ala Ser
1               5                   10                  15

Asp Asp Tyr Gly Lys Asp Leu Thr Asn Val Gln Asn Leu Gln Lys Lys
            20                  25                  30

His Ala Leu Leu Glu Ala Asp Val Ala Ala His
        35                  40

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly His Phe Asp Ala Glu Asn Ile Lys Lys Lys Gln Glu Ala Leu
1               5                   10                  15

Val Ala Arg Tyr
            20

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Arg Ile Thr Lys Glu Ala Gly Ser Val Ser Leu Arg Met Lys Gln
1               5                   10                  15

Val Glu Glu Leu Tyr His Ser Leu Leu Glu
            20                  25

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Glu Lys Ser Cys Lys Lys Phe Met Leu Phe Arg Glu Ala Asn Glu
1               5                   10                  15

Leu Gln Gln Trp Ile Asn Glu Lys Glu Ala Ala Leu Thr Ser Glu Glu
            20                  25                  30

Val Gly Ala Asp Leu Glu Gln Val Glu Val Leu Gln
        35                  40

<210> SEQ ID NO 14
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid

<400> SEQUENCE: 14

Glu Gly Leu Met Ala Glu Glu Val Gln Ala Val Gln Gln Gln Glu Xaa
1               5                  10                  15

Tyr

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Met Met Pro Arg Asp Glu Thr Asp Ser Lys Thr Ala Ser Pro Trp
1               5                  10                  15

Lys Ser Ala Arg Leu Met Val His Thr Val Ala Thr Phe Asn Ser Ile
            20                  25                  30

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid

<400> SEQUENCE: 16

Glu Gly Leu Met Ala Glu Glu Val Gln Ala Val Gln Gln Gln Glu Xaa
1               5                  10                  15

Tyr Gly Met Met Pro Arg Asp Glu Thr Asp
            20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Lys Thr Ala Ser Pro Trp Lys Ser Ala Arg Leu Met Val His Thr
1               5                  10                  15

Val Ala Thr Phe Asn Ser Ile
            20

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 18

Thr Glu Ile Asp Ala Arg Ala Gly Thr Phe Gln Ala Phe Glu Gln Phe
1               5                   10                  15

Gly Gln Gln Leu Leu Ala His Gly His Tyr Ala Ser Pro
            20                  25

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Thr Glu Asp Lys Gly Asp Ser Leu Asp Ser Val Glu Ala Leu Ile
1               5                   10                  15

Lys

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Val Glu Ala Leu Ile Lys Lys His Glu Asp Phe Asp Lys Ala Ile
1               5                   10                  15

Asn Val Gln Glu Glu
            20

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Glu Gln Ala Glu Asn Trp Met Ala Ala Arg Glu Ala Phe Leu Asn
1               5                   10                  15

Thr Glu Asp Lys Gly Asp Ser Leu Asp
            20                  25

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ile Ala Ala Leu Gln Ala Phe Ala Asp Gln Leu Ile Ala Ala Gly
1               5                   10                  15

His Tyr Ala Lys
            20

<210> SEQ ID NO 23
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 23

Ile Glu Arg Gly Ala Cys Ala Gly Ser Glu Asp Ala Val Lys Ala Arg
1               5                   10                  15

Leu Ala Ala Leu Ala Asp Gln Trp Gln Phe Leu Val Gln Lys
            20                  25                  30

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Phe Trp Leu Ser Glu Val Glu Ala Leu Leu Ala Ser Glu Asp Tyr
1               5                   10                  15

Gly Lys Asp Leu Ala Ser Val Asn
            20

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Asn Asn His His Glu Glu Asn Ile Ser Ser Lys Met Lys Gly Leu
1               5                   10                  15

Asn Gly Lys Val Ser Asp Leu Glu Lys
            20                  25

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Thr Asp Asp Tyr Gly Arg Asp Leu Ser Ser Val Gln Thr Leu Leu
1               5                   10                  15

Thr

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Leu Lys Asp Gln Leu Leu Ala Ala Lys His Val Gln Ser Lys
1               5                   10                  15
```

-continued

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Thr Asp Pro Val Arg Cys Asn Ser Leu
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Pro Thr Ala Phe Asp Tyr Val Glu Phe Thr Arg Ser Leu Phe Val
1               5                   10                  15

Asn

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Lys Gly Leu Ala Leu Gln Arg Gln
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Ala Ser Asp Val Ala Gly Ala Glu Ala Leu Leu Asp Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Tyr Glu Gln Cys Met Asp Leu Gln Leu Phe Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 33

Ala Ala Glu Asp Val Lys Ala Lys Leu His Glu
1               5                  10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Glu Ala Leu Leu Lys Lys His
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ile Asn Lys Val Ala Glu
1               5

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Gln Leu Leu Gly Ser Ala His Glu Val Gln Arg
1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly His Asp Leu Ala Ser Val Gln Ala Leu Gln
1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Asp Leu Ala Ala Leu Gly Asp Lys Val Asn Ser
1               5                  10

<210> SEQ ID NO 39
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 39

Met Leu Asp Gln Cys Leu Glu Leu Gln Leu Phe His Arg Asp
1               5                   10

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Lys Asp Leu Ala Ser Val Asn Asn Leu Leu Lys Lys His Gln Leu
1               5                   10                  15

Leu Glu Ala Asp Ile
            20

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Ala Glu Leu Ala Ala His Glu Pro Ala Ile Gln Gly Val Leu
1               5                   10                  15

Asp Thr

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Gln Gln Arg Leu Ala Gln Phe Val Glu His
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Lys Ala Asp Val Val Glu Ser
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 44

Ala Leu Ile Leu Asp Asn
1               5

<210> SEQ ID NO 45
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Any amino acid

<400> SEQUENCE: 45

Asn Lys Val Ala Glu Asp Leu Glu Ser Glu Gly Leu Met Ala Glu Glu
1               5                   10                  15

Val Gln Ala Val Gln Gln Gln Xaa Tyr Gly Met Met Pro Arg Asp
            20                  25                  30

Glu Thr Asp Ser Lys Thr Ala Ser Pro Trp Lys Ser Ala Arg Leu Met
        35                  40                  45
```